(12) United States Patent
Mercati et al.

(10) Patent No.: US 11,612,628 B2
(45) Date of Patent: Mar. 28, 2023

(54) COMPOSITIONS FOR THE TREATMENT OF ARTICULAR DISORDERS

(71) Applicant: Aboca S.p.A. Società Agricola, Sansepolcro (IT)

(72) Inventors: Valentino Mercati, Sansepolcro (IT); Carla Ghelardini, Sansepolcro (IT); Lorenzo Di Cesare Mannelli, Sansepolcro (IT)

(73) Assignee: Aboca S.p.A. Società Agricola, Sansepolcro (IT)

( * ) Notice: Subject to any disclaimer, the term of this patent is extended or adjusted under 35 U.S.C. 154(b) by 0 days.

(21) Appl. No.: 16/477,650

(22) PCT Filed: Jan. 26, 2018

(86) PCT No.: PCT/IB2018/050480
§ 371 (c)(1),
(2) Date: Jul. 12, 2019

(87) PCT Pub. No.: WO2018/138678
PCT Pub. Date: Aug. 2, 2018

(65) Prior Publication Data
US 2019/0358280 A1 Nov. 28, 2019

(30) Foreign Application Priority Data
Jan. 26, 2017 (IT) .................. 102017000008696

(51) Int. Cl.
| | |
|---|---|
| *A61K 36/23* | (2006.01) |
| *A61P 19/02* | (2006.01) |
| *A61K 9/00* | (2006.01) |
| *A61K 9/19* | (2006.01) |
| *A61K 36/28* | (2006.01) |
| *A61K 47/02* | (2006.01) |
| *A61K 47/10* | (2017.01) |
| *A61K 47/12* | (2006.01) |
| *A61K 47/14* | (2017.01) |
| *A61K 47/18* | (2017.01) |
| *A61K 47/26* | (2006.01) |

(52) U.S. Cl.
CPC .......... *A61K 36/23* (2013.01); *A61K 9/0019* (2013.01); *A61K 9/19* (2013.01); *A61K 36/28* (2013.01); *A61K 47/02* (2013.01); *A61K 47/10* (2013.01); *A61K 47/12* (2013.01); *A61K 47/14* (2013.01); *A61K 47/183* (2013.01); *A61K 47/186* (2013.01); *A61K 47/26* (2013.01); *A61P 19/02* (2018.01)

(58) Field of Classification Search
CPC ........ A61K 36/23; A61K 9/0019; A61K 9/19; A61K 36/28; A61K 47/02; A61K 47/10; A61K 47/12; A61K 47/14; A61K 47/183; A61K 47/186; A61K 47/26; A61P 19/02
See application file for complete search history.

(56) References Cited

U.S. PATENT DOCUMENTS

| | | | |
|---|---|---|---|
| 2004/0023894 A1* | 2/2004 | Hasler-Nguyen | A61K 36/889 514/27 |
| 2005/0002962 A1* | 1/2005 | Pasco | A61K 36/71 424/737 |
| 2007/0071840 A1 | 3/2007 | Dhanaraj et al. | |

FOREIGN PATENT DOCUMENTS

| | | | |
|---|---|---|---|
| DE | 19908441 C1 | 8/2000 | |
| WO | WO-2009078022 A2 * | 6/2009 | ............. A61K 36/28 |
| WO | WO-2018138678 A1 | 8/2018 | |

OTHER PUBLICATIONS

Ganachari et al., "Neuropharmacology of an Extract Derived from Centella asiatica" Pharmaceutical Biology, 2004, vol. 42, No. 3, pp. 246-252. (Year: 2004).*

Arafa, N.M.S., et al., "The effectiveness of Echinacea extract or composite glucosamine, chondroitin and methyl sulfonyl methane supplements on acute and chronic rheumatoid arthritis rat model," *Toxicology and Industrial Health* 29(2):187-201, Sage Publications Ltd., United Kingdom (2013).

International Search Report and Written Opinion for International Application No. PCT/IB2018/050480, European Patent Office, Netherlands, dated Apr. 20, 2018, 11 pages.

* cited by examiner

*Primary Examiner* — Aradhana Sasan
(74) *Attorney, Agent, or Firm* — Sterne, Kessler, Goldstein & Fox P.L.L.C.

(57) ABSTRACT

The present invention relates to new compositions suitable for use in the treatment of articular disorders (or conditions), processes for preparing said compositions and use of said compositions in therapeutic treatments of articular disorders.

25 Claims, 22 Drawing Sheets

Figure 1G:
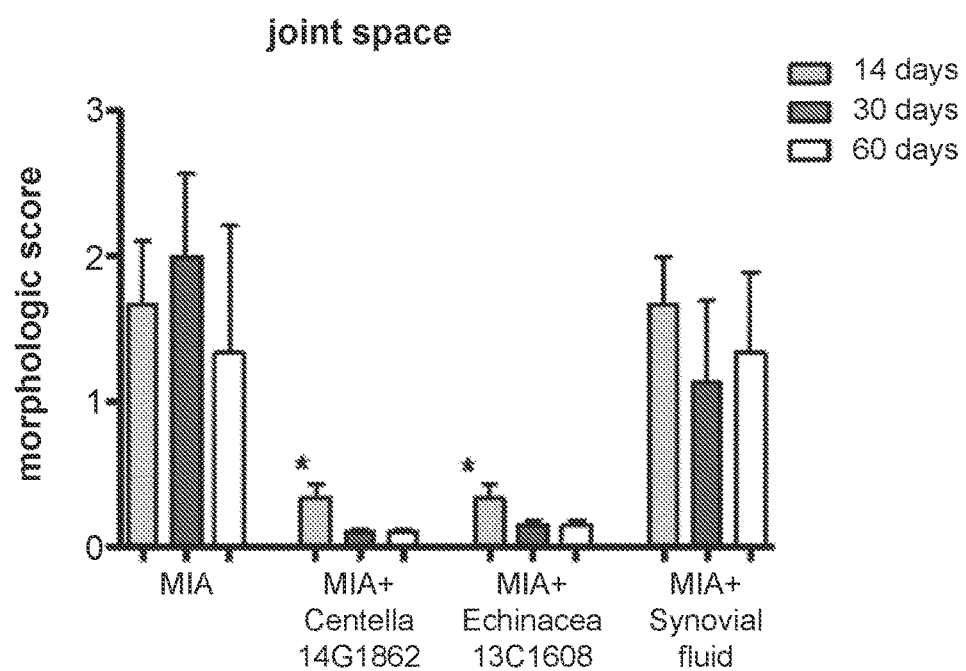

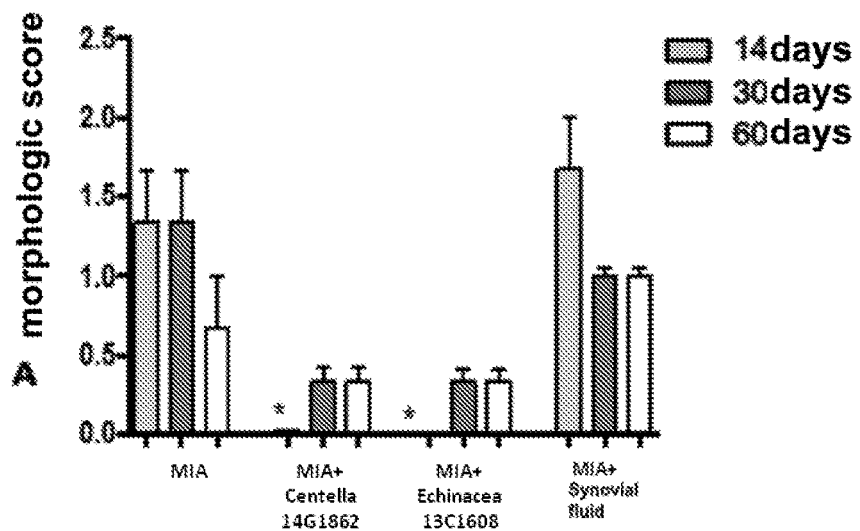
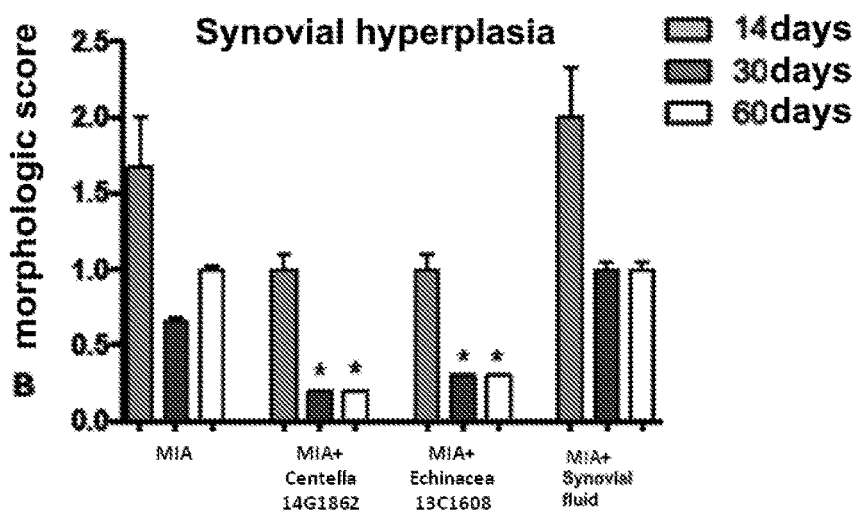
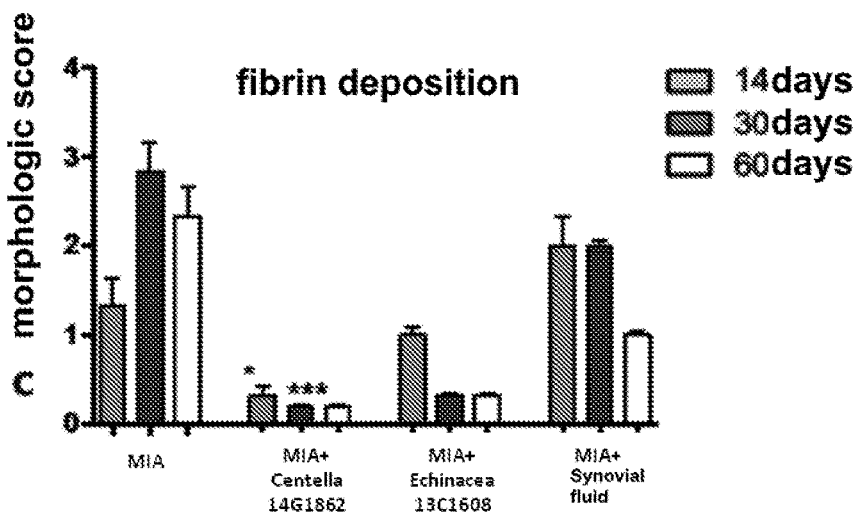
Fig. 1 A-C

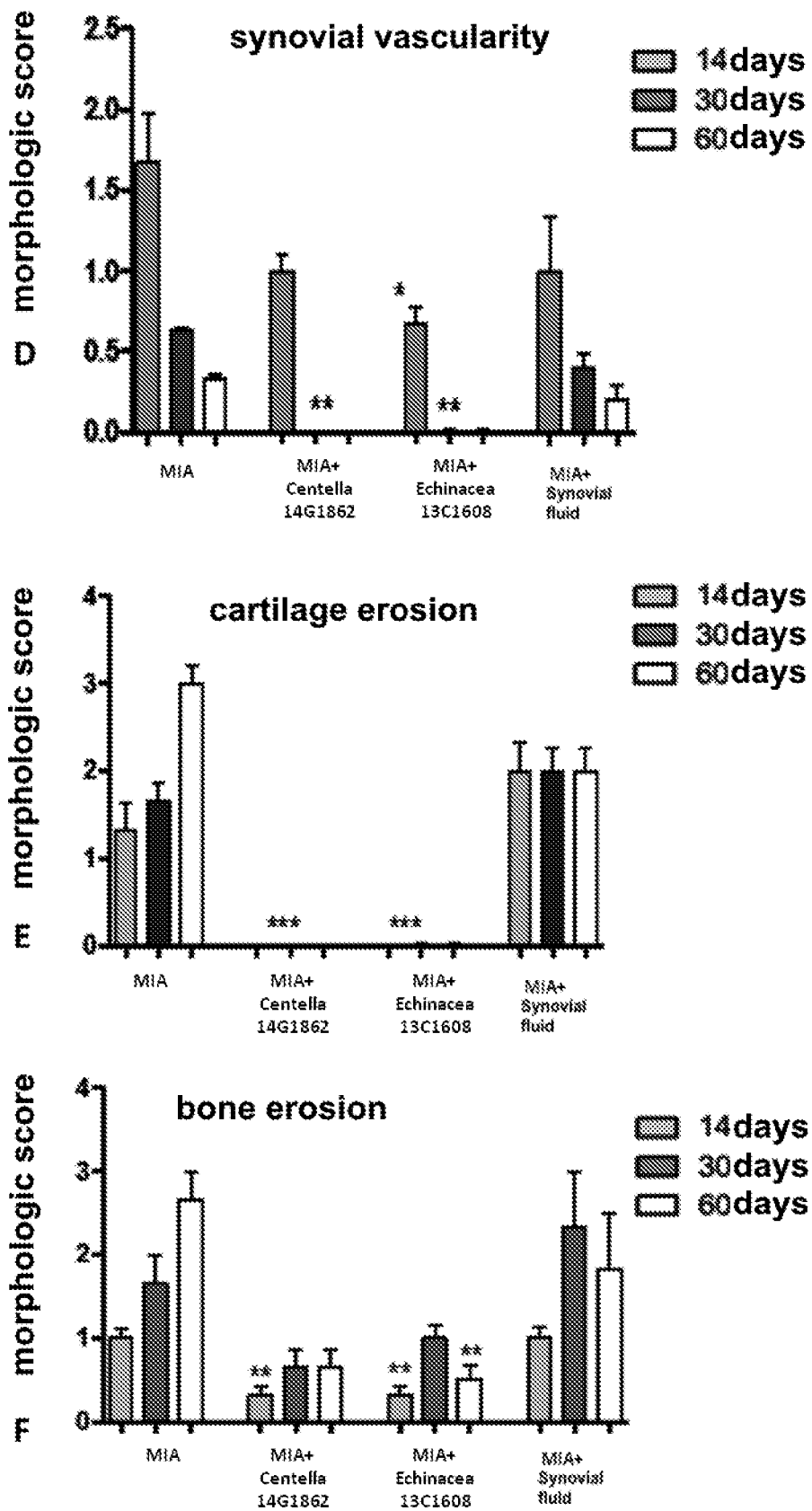
Fig. 1 D-F

Figure 3G:
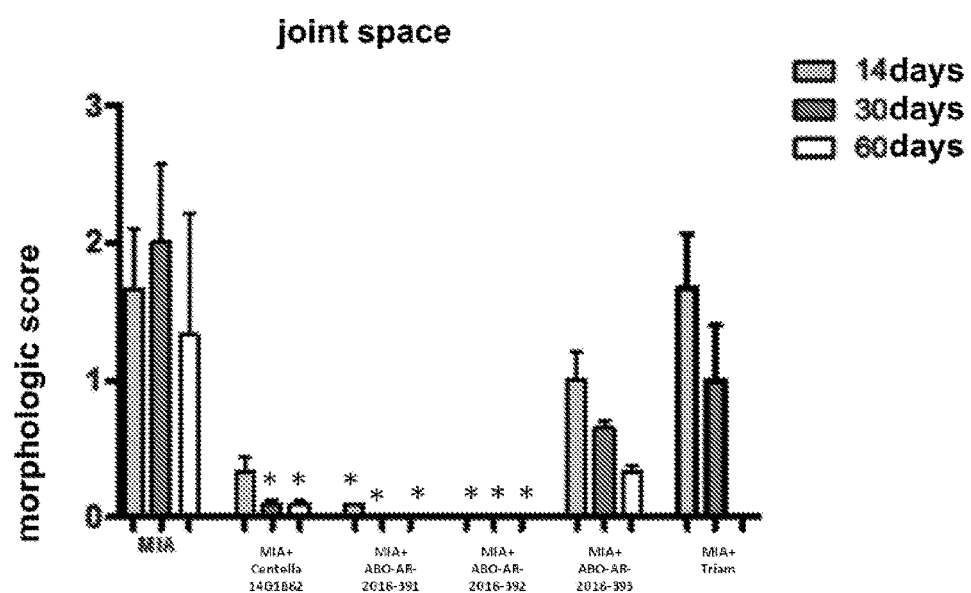

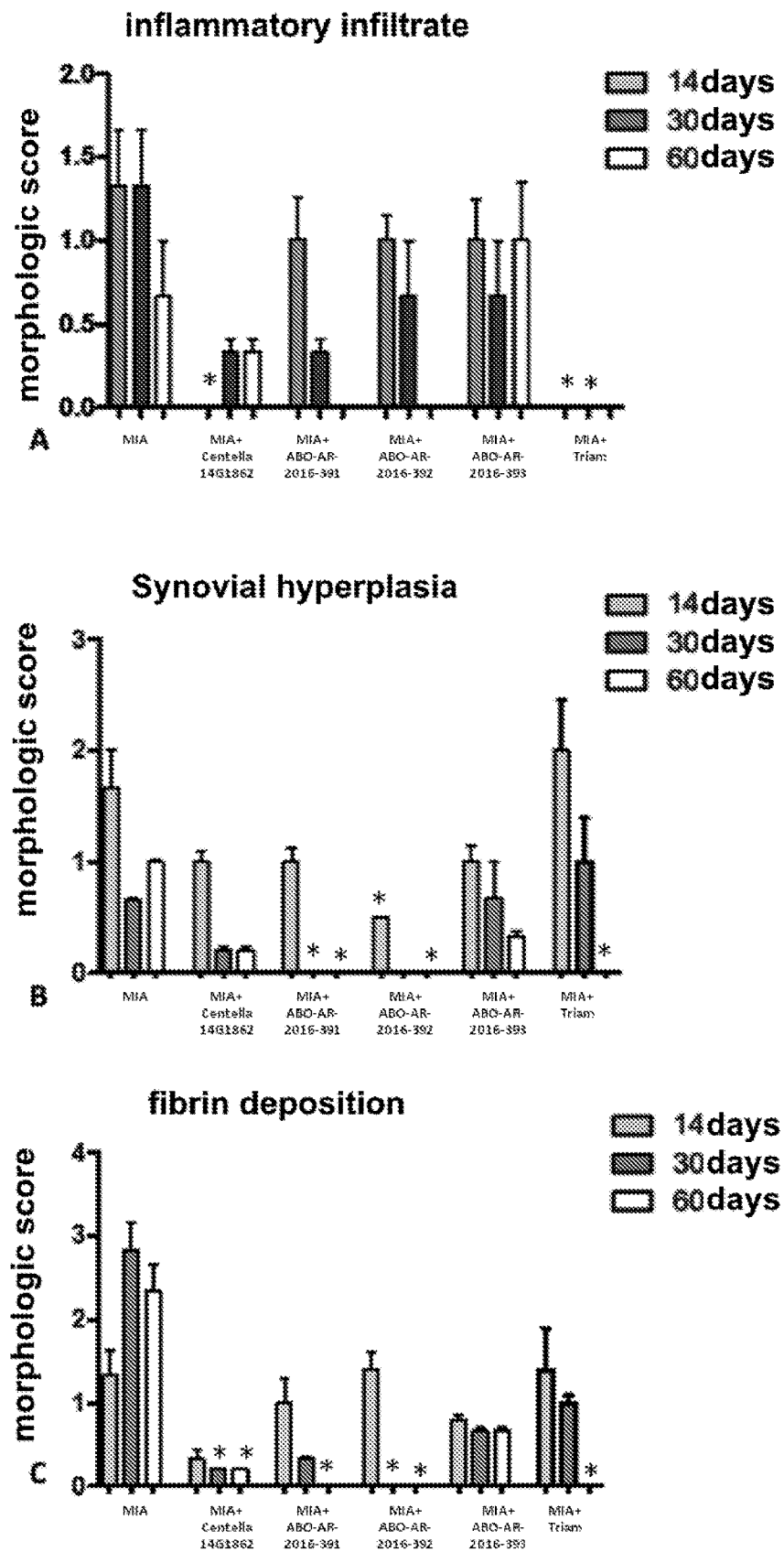
Fig. 3 A-C

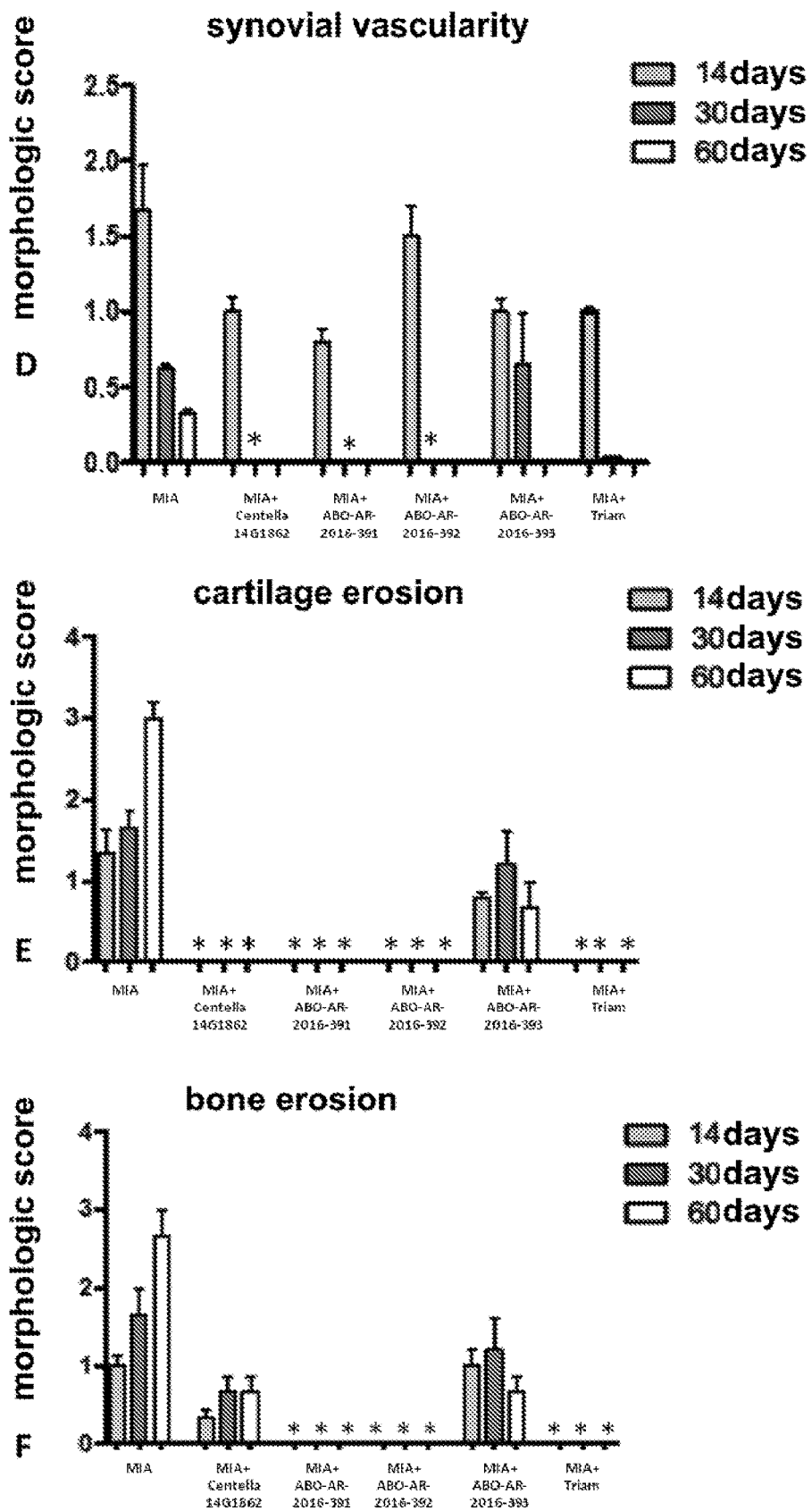
Fig. 3 D-E

Figure 18:
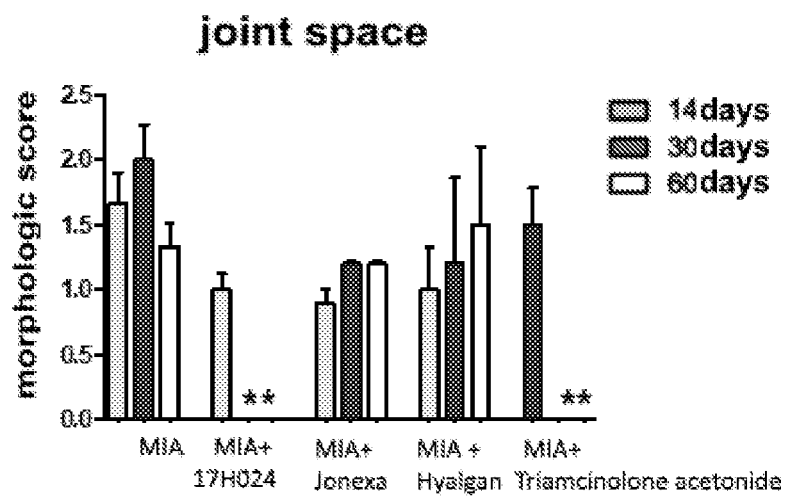

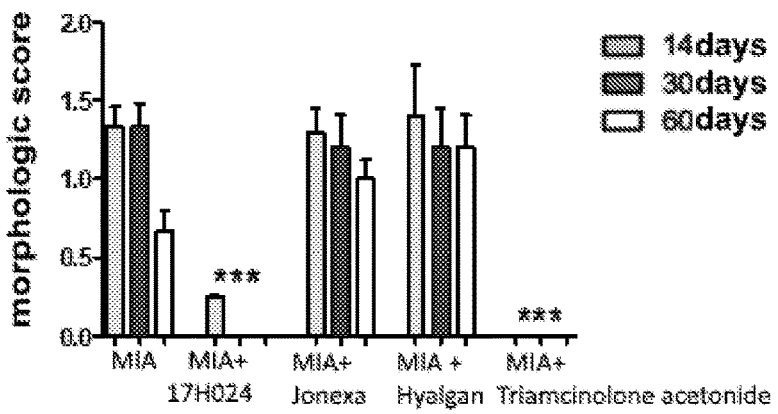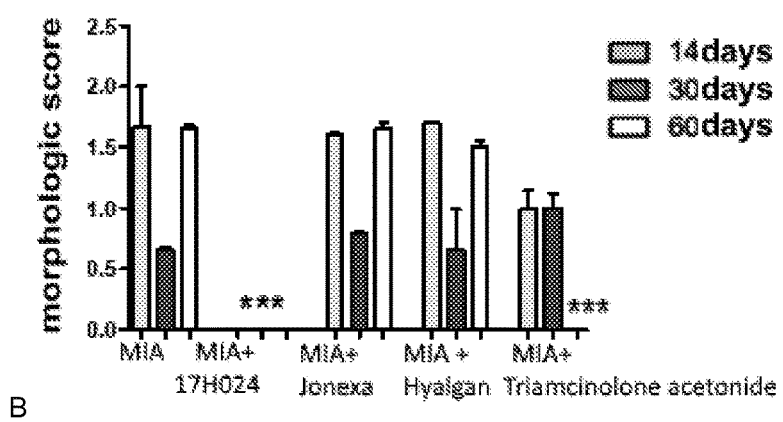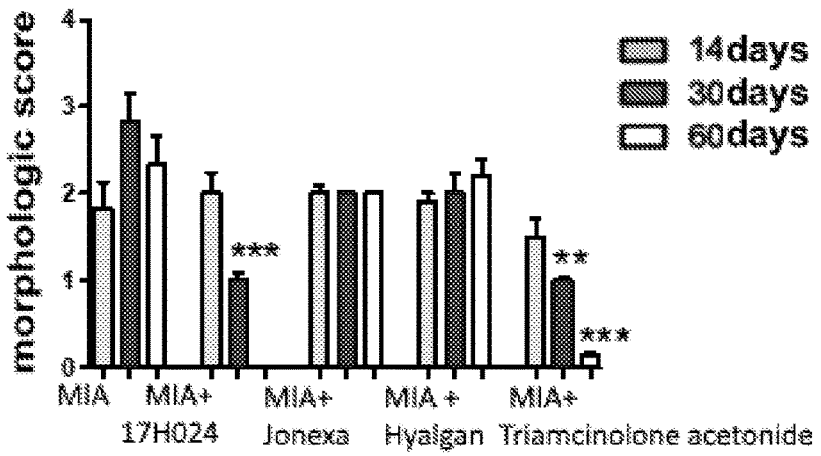
Fig 18 A-C

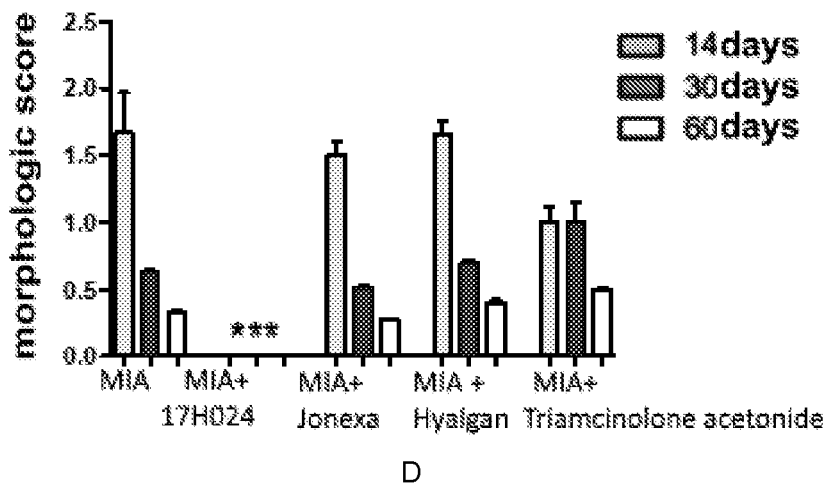
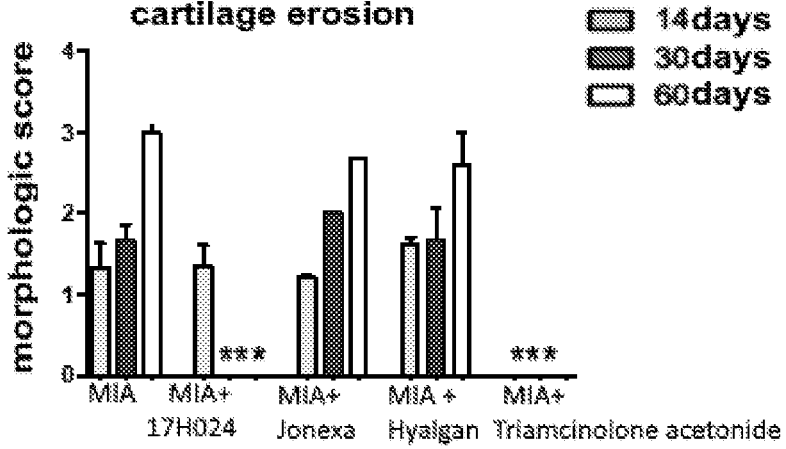
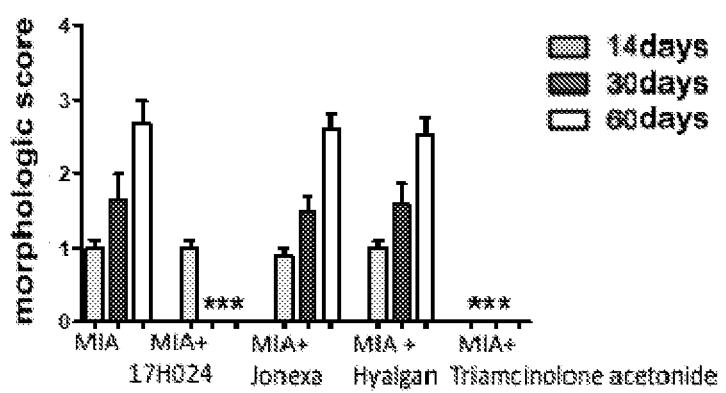
Fig 18 D-F

COMPOSITIONS FOR THE TREATMENT OF ARTICULAR DISORDERS

The present invention relates to new compositions suitable for use in the treatment of articular disorders, processes for preparing said compositions and use of said compositions in therapeutic treatments of articular disorders.

STATE OF THE PRIOR ART

Articular cartilage plays a key role in the movement of human and animal joints. It provides a smooth upper surface between adjacent bones, enabling nearly frictionless movement of the joints. Synovial fluid inside the joint cavity acts as a lubricant. In joints, articular cartilage distributes compressive stresses on the surfaces of the articular plates of the joint, thereby protecting load-bearing bones from rubbing and deterioration. Articular cartilage is comprised of chondrocytes embedded into an extracellular matrix of proteoglycans, collagen, glycosaminoglycans and low-molecular-weight (MVV) glycoproteins. Chondrocytes are cartilage cells embedded in lacunae inside the cartilage matrix. Proteoglycans are essential to preserve cartilage tissue strength, so that it may resist compression. Collagen gives to the tissue tensile strength and resistance to shearing stress. In a healthy joint, the extracellular matrix is maintained by an equilibrium between synthesis and secretion of these macromolecules by chondrocytes, and their subsequent degradation by proteolytic enzymes. Damages to cartilage of the articular surface can upset this balance, so that degradation overcomes chondrocytes' ability to synthesize macromolecules required for cartilage tissue repair. Chronic imbalance of the equilibrium between synthesis and degradation of cartilage matrix macromolecules is associated with development of osteoarthritis.

Osteoarthritis (OA) is a degenerative disorder involving joints. In veterinary medicine it is also known as Degenerative Joint Disease (DJD). It is the commonest form of arthritis and results from progressive cartilage degeneration which accompanies ageing. Typically, OA manifests itself following traumas or chronic joint lesions due to other types of arthritis, such as rheumatoid arthritis. Alternatively, OA may ensue from excessive use of a specific joint. OA can be classified as: primary, in which no underlying cause is evident; secondary, when a predisposing factor is associated therewith, such as trauma, repetitive stress (occupation, sport), congenital anomalies, metabolic diseases (disorders), or other bone/articular disease (disorder); and erosive, which is characterized by periods of acute inflammation and progressive destruction of the joints, occurring more often in middle-aged women. OA is more widespread in the joints of finger, hip, knee, spine, thumb and hallux base. Clinically, OA is characterized by articular pain, limitation of movement, crepitus (crackling), and inexorable progressive disability. It may be present in only one of these joints, or in all. Though most body tissues are able to repair themselves following an accident, cartilage self-repair is hindered by a limited blood supply and the lack of an effective mechanism for cartilage replacement.

Historically, treatment of osteoarthritis and articular cartilage lesions has been limited to symptomatic pain relief therapies, reduction of articular load, physical therapies, and orthopedic surgery. Most of these therapies aim at relieving the symptoms, rather than treating the underlying pathological condition. More recently, research has focused on the development of chondroprotective methods. Such methods envisage long-term therapeutic treatment aimed at preserving or stimulating cartilage formation. The current treatment of arthritis comprises first-line drugs for pain and inflammation control, classified as non-steroidal anti-inflammatory drugs (NSAIDs), such as, e.g., aspirin, ibuprofen and naproxen. Secondary treatments include corticosteroids, which act as slow-acting anti-rheumatic drugs (SAARDs) or disease-modifying anti-rheumatic drugs (DMARDs), e.g., penicillamine, cyclophosphamide, gold salts, azathioprine and levamisole for rheumatoid arthritis.

Even though NSAIDs are one of the main groups of drugs used in OA management, their side effects are often considered not advantageous in terms of risk/benefit ratio, particularly in the elderly. Depending on individual circumstances, NSAIDs can cause gastrointestinal (GI) hemorrhage, GI mucosa ulceration or perforation, whereas some are cause of bone marrow depression, or retention of liquids, and can contribute therefore to kidney failure. These effects are particularly relevant, since such treatments are often long-term. Moreover, the use of officinal plants for treating a variety of disorders (or conditions) in mammals is known.

Another approach used in the treatment of osteoarthritis and of the various forms of arthrosis is viscosupplementation. Said treatment is performed by infiltrating a therapeutic solution in the joint, usually comprising hyaluronic acid.

Although the above-mentioned drugs and treatments have met a certain degree of success in the preventive treatment of osteoarthritis, new therapeutic solutions which may effectively reduce lesion progression and cartilage degradation in a mammal suffering from osteoarthritis are constantly being sought. Therefore, object of the present invention is to provide a method for the effective treatment of arthritis, degenerative diseases (disorders) of intervertebral discs, rheumatoid arthritis and cartilage diseases.

SUMMARY OF THE INVENTION

The Authors of the present invention have surprisingly discovered that some substances, in specific concentrations, or mixtures thereof, have an effective therapeutic effect in the treatment of disorders (or conditions) affecting articular cartilage in mammals. The figures appended to the present description, and the experiments carried out by the Authors and reported below, show the effectiveness of the substances and combinations claimed.

Therefore, object of the present invention is a parenteral composition comprising an extract or one or more fractions of *Centella asiatica* and/or an extract or one or more fractions of *Echinacea purpurea*, and at least one pharmaceutically acceptable carrier, the therapeutic use of said composition and processes for preparing the same.

DETAILED DESCRIPTION OF THE FIGURES

FIG. 1 reports, in the various panels, the histological state of rat joints treated with monoiodine acetate (MIA) and subsequently with the sole vehicle (carrier) (denoted by MIA alone), with extract of *Centella*, fraction soluble in 70% hydroalcoholic solution (MIA+*Centella* 14G1862), with extract of *Echinacea purpurea* fraction soluble in 40-50% hydroalcoholic solution, (MIA+*Echinacea* 13C1608) and with bovine synovial fluid (MIA+synovial fluid) at 14, 30 and 60 days.

In panel a, the morphological score attributed to the inflammatory infiltrate (a high score corresponds to a high presence of inflammatory infiltrate), in panel b, the score attributed to synovial hyperplasia, in panel c, that attributed to fibrin deposition, in panel d, that attributed to synovial vascularity, in panel e, that attributed to cartilage erosion, in panel f, that attributed to bone erosion, and, in panel g, that attributed to the reduction (narrowing) of the space between the two ends of the joint are reported (in this latter case a high score corresponds to a reduced joint space). MIA-treated animals exhibit, at articular level, the presence of inflammatory infiltrate (MIA; panel a) and a morphological damage highlighted by development of synovial hyperplasia (MIA; panel b) and increased vascularity (MIA; panel d), reaching a maximum level at day 14 and progressively tending to reduce in the course of days. Cartilage and bone erosion (MIA; panels e-f), fibrin deposition (MIA; panel c) and joint space reduction (MIA; panel g) show instead a time-dependent increase until day 30. The treatment with the extract (above-described fraction) of *Centella* and of *Echinacea* effectively opposes MIA-induced morphological damage, keeping low the scores of most of the evaluated parameters (panels a-g), whereas synovial fluid does not prove effective in MIA-damaged joint protection (panels a-g).

Figure 2:
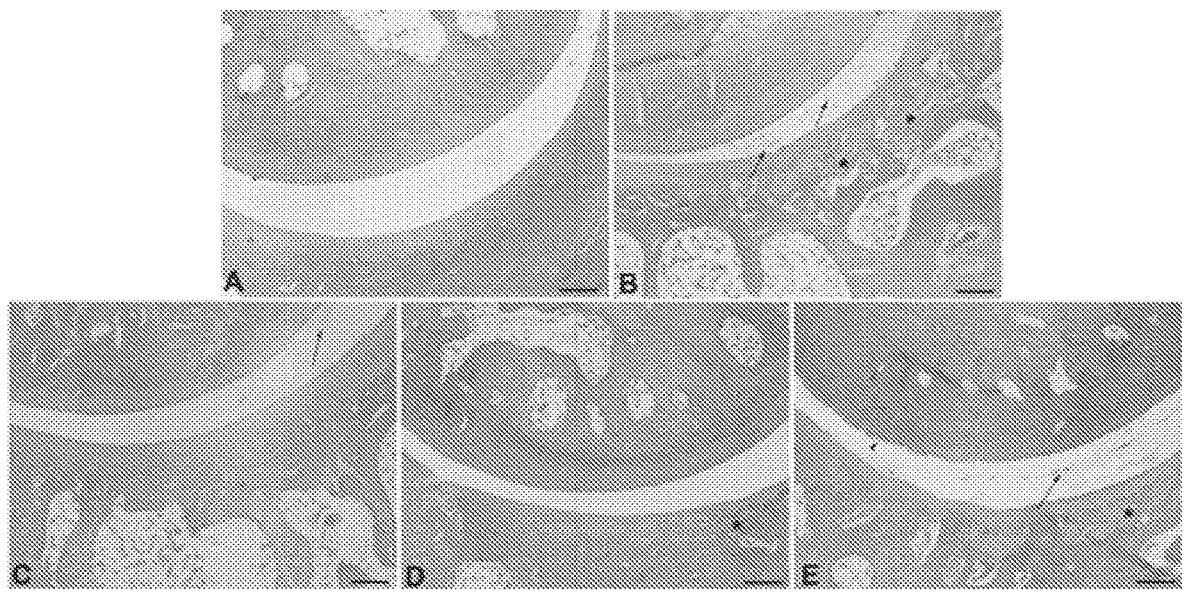

FIG. 2 reports the overall histological scene: A Control; B MIA; C MIA+Hyalgan; D MIA+*Centella* 14G1862; E MIA+*Echinacea* 13C1608; F MIA+bovine synovial fluid. In the treated animals' image, it is possible to highlight fibrin deposition in the articular space (black arrows), cartilage erosion (black arrowheads) and bone erosion (asterisks). Calibration bar: 100 μm.

FIG. 3 reports in the different panels, the histological state of rat joints treated with monoiodine acetate (MIA) and subsequently with sole vehicle (denoted as MIA alone), with extract of *Centella*, fraction soluble in EtOH 70% (MIA+*Centella* 14G1862), with extract of *Centella*, insoluble fraction, solubilized in EtOH 13% (MIA+ABO-AR-2016-391), with extract of *Centella*, filtered fraction −391, permeate (MIA+ABO-AR-2016-392), with extract of *Centella*, filtered fraction −391, retentate (MIA+ABO-AR-2016-393) and with Triamcinolone acetonide (MIA+Triam) at 14, 30 and 60 days.

In panel a, the morphological score attributed to the inflammatory infiltrate (a high score corresponds to a high presence of inflammatory infiltrate) is reported, in panel b, the score attributed to synovial hyperplasia, in panel c, that attributed to fibrin deposition, in panel d, that attributed to synovial vascularity, in panel e, that attributed to cartilage erosion, in panel f, that attributed to bone erosion, and, in panel g, that attributed to the reduction of the space between the two ends of the joint are reported (in this latter case a high score corresponds to a reduced joint space). MIA-treated animals exhibit, at articular level, the presence of inflammatory infiltrate (MIA; panel a) and a morphological damage highlighted by development of synovial hyperplasia (MIA; panel b) and increased vascularity (MIA; panel d) reaching a maximum level at day 14 and/or 30, tending to progressively reduce in the course of days. Cartilage and bone erosion (MIA; panels e-f), fibrin deposition (MIA; panel c) and joint space reduction (MIA; panel g) exhibit instead a time-dependent increase up to day 30 (MIA; panels c,g), or up to day 60 (MIA; panels e-f). From the figure it is inferred how the fractions of *Centella* 14G1862, ABO-AR-2016-391 and ABO-AR-2016-392 be able to protect the joint from MIA-induced damage in many of the parameters assessed. Instead, fraction ABO-AR-2016-393 is not particularly effective (MIA+ABO-AR-2016-392; panels a-g), whereas the drug Triamcinolone only partially reduces the damaging effects of MIA (MIA+Triam; panels a,b,c,e,f).

Figure 4:
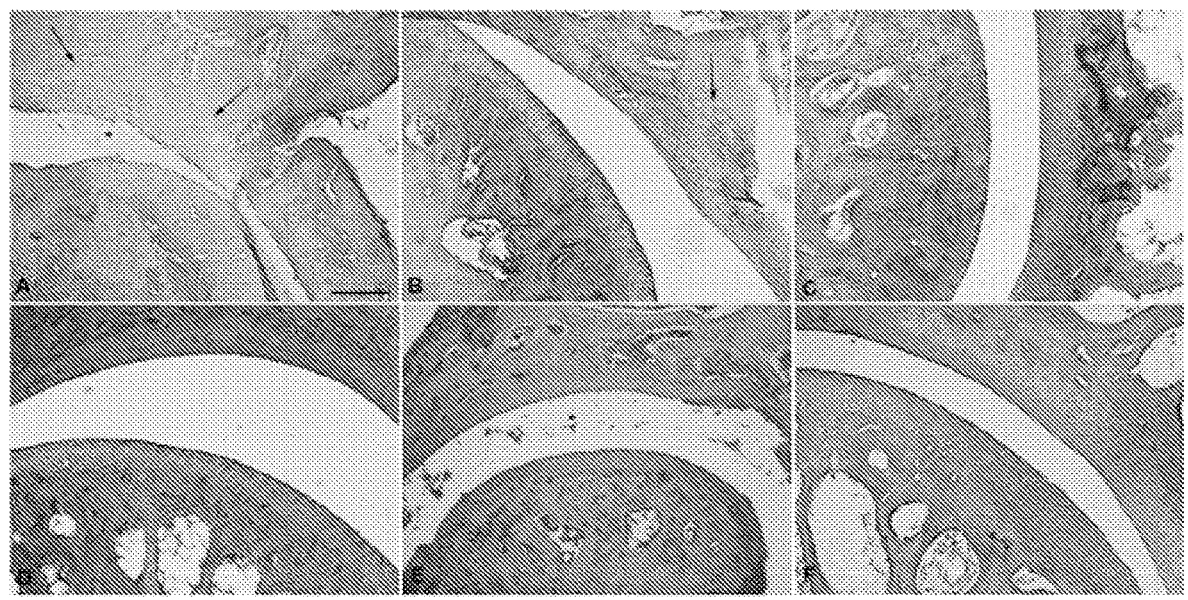

FIG. 4 reports the overall histological scene: A: MIA; B: MIA+*Centella* 14G1862; C: MIA+ABO-AR-2016-391; D: MIA+ABO-AR-2016-392; E: MIA+ABO-AR-2016-393; F: MIA+Triamcinolone. In the images of treated animals, there can be highlighted fibrin deposition in the articular space (asterisk), cartilage erosion (black arrows). Calibration bar: 100 μm.

FIGS. 5-13 graphically depict data reported in Tables 1 to 9. In the figures and text, the MIX (coextract) lot 17H0246 corresponds to a mixture of extract of *Echinacea*, fraction soluble in hydroalcoholic solution according to the present description, lyophilized, and extract of *Centella asiatica*, fraction soluble in hydroalcoholic solution according to the present description, resuspended with NaCl in water, incubated at 40-55° C. for 4-8 hours, filtered and lyophilized.

FIG. 14-17: the mixture of the invention was assayed in separate experiments relative to the individual fractions of *Centella* and *Echinacea*. Behavioral test data were therefore expressed as % of improvement compared to their positive control (MIA-treated animal+vehicle), so as to obtain a numerical value indicative of animal improvement after the treatment. Thus, it is possible to compare the effect of the treatments: said % value enables to quantitate the higher or lower effectiveness of a sample compared to the other one. FIGS. 14-17 graphically report the results of said comparisons.

FIG. 18 reports, in the various panels, the histological state of rat joints treated with monoiodine acetate (MIA) and subsequently with sole vehicle (denoted as MIA alone), with MIX (coextract) *Centella*+*Echinacea* lot 17H0246, Hyalgan, Jonexa and Triamcinolone acetonide at 14, 30 and 60 days.

In panel a, the morphological score attributed to the inflammatory infiltrate (a high score corresponds to a high presence of inflammatory infiltrate), in panel b, the score attributed to synovial hyperplasia, in panel c, that attributed to fibrin deposition, in panel d, that attributed to synovial vascularity, in panel e, that attributed to cartilage erosion, in panel f, that attributed to bone erosion, and, in panel g, that attributed to the reduction of the space between the two articular ends are reported (in this latter case a high score corresponds to a reduced joint space).

Figure 19:
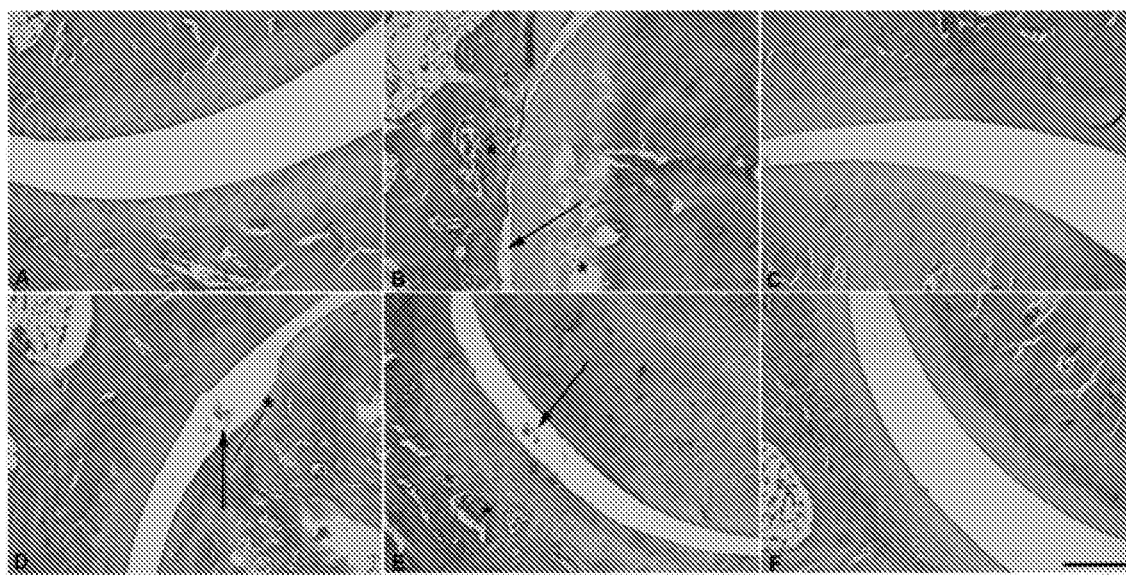

FIG. 19 reports the overall histological scene: images representative of the histological scene detectable at 30 days: A: Control; B: MIA; C: MIA+MIX (coextract) *Centella*+*Echinacea* lot 17H0246; D: MIA+Jonexa; E: MIA+Hyalgan; F: MIA+triamcinolone acetonide. In the treated animals' images, it is possible to highlight fibrin deposition in the articular space (black arrows), erosion of cartilage of encrustment and of subchondral bone (asterisks). Calibration bar:100 μM.

The term coextract lot 17H0246 in the caption of the figures and in the tables refers to the fact that the extract of *Centella* and that of *Echinacea* are mixed and subjected to a further step of extraction in aqueous solution before being used in the end composition, as described below in the present description.

DETAILED DESCRIPTION OF THE INVENTION

The present invention relates to a parenteral composition comprising an extract of *Centella asiatica*, an extract of *Echinacea purpurea*, and at least one pharmaceutically acceptable carrier.

For the purposes of the present invention, by "parenteral composition" it is meant a composition that can be introduced in the body by piercing the coating tissues with a needle, so as to be able to get into various cavities, organs or tissues. For the purposes of the present invention, the composition will in particular be an intraarticular composition, i.e., a composition suitable for injection directly into the joint.

For the purposes of the present invention, by the term "extract" it is meant a preparation in fluid, solid or soft form coming from parts of fresh or dried plants, obtainable by suitable extraction processes, e.g. with appropriate solvents and/or by soaking, percolation, filtering, and other suitable processes.

As is known, extraction processes from plant drugs can comprise plural stages, and consequently, at the end or during the extraction process, plural different fractions can be obtained, therefore, by the term "extract" according to the invention, there are also meant the individual fractions obtainable during the extraction process, or mixtures thereof. In any point of the present description and of the claims, therefore, the term extract may be replaced by the term fraction of extract or mixture of fractions of extract.

According to one embodiment of the invention, the extract of Centella asiatica can be, e.g., prepared from crumbled Centella leaves that are subjected to soaking in alcohol (from 65% to 75%) at about 65%, about 70%, about 75% (non-limiting example: ethanol:water 70:30 v/v). In one exemplary embodiment, the extract of Centella is obtained with a 1:8 ratio between Centella and alcohol 70%, at a suitable extraction temperature, comprised between 40 and 60° C. Extraction is normally protracted for 6-8 hours, then the spent residue is separated from the solution by decanting and subsequent filtering (e.g., on paper filter).

In one embodiment, the extract (more precisely, the resulting hydroalcoholic fraction) is subjected to concentration and drying by lyophilization, according to methodologies known to a technician in the field.

In one embodiment of the invention, therefore, the term "extract" corresponds to a fraction soluble in hydroalcoholic solution as above exemplified.

In some of the examples reported in the present description, representing embodiments of the invention, the extract of Centella reported in the figures and tables as Centella 14G1862 is a fraction of aerial parts of the plant soluble in hydroalcoholic solution prepared as reported above.

According to a further embodiment of the present invention, the fractions of Centella asiatica soluble in hydroalcoholic solution can also be fractions prepared by subjecting the part of interest of the plant to a first extraction with a suitable alcohol at about 96% (e.g., ethanol:water 96:4 v/v) in a ratio between drug and alcohol 96% of about 1:8, at a suitable temperature, comprised between 30 and 50° C. for a period of time from 6 to 8 hours.

After said period of time the supernatant is removed, and the residual drug is subjected to a further extraction with a suitable alcohol at about 13% (e.g., ethanol:water 13:87 v/v) in a ratio between drug and alcohol 13% of 1:8, at a suitable temperature, comprised between 30 and 50° C. for a period of time from 6 to 8 hours. Thereafter, the solid residue is discarded by decanting and filtering on paper, whereas the resulting 13% alcoholic fraction is collected.

In one embodiment, the extract is represented by said 13% alcoholic fraction which is subjected to alcohol evaporation and subsequently to filtering on paper, to provide a clear aqueous concentrate which is dried by lyophilization, according to technique known to an expert in the field (e.g., fraction ABO-AR-2016-391 according to the present description).

Furthermore, a part of the aqueous concentrate prepared above can be passed on a molecular exclusion membrane to provide a permeate fraction and a retentate fraction. In one embodiment, said fractions are subjected to concentration and drying by lyophilization, according to methodologies known to a person skilled in the art. Examples of fractions according to this embodiment are the permeate fraction ABO-AR-2016-392 and the retentate fraction ABO-AR-2016-393 as reported in the present description.

According to the present description, the following membranes can be used: molecular filtration membrane characterized by a MWCO (molecular weight cutoff) of 150-300 Da, or alternatively of 700 Da, or alternatively of 1000 Da, or alternatively of 2500 Da, or alternatively of 5000 Da, or alternatively of 10000 Da, or alternatively of 20000 Da, or alternatively of 50000 Da. Said membranes may be spiral-like, wound in a polyamide, polysulfone, polyethersulfone material, or in ceramics.

In one embodiment of the invention, the extract of Echinacea purpurea could be prepared by extraction in hydroalcoholic solution of crumbled aerial parts of Echinacea, e.g. in a suitable hydroalcoholic solution with alcohol between 40 and 55%, e.g. at about 40%, about 45%, about 50%, about 55% (e.g., in a non-limiting manner, ethanol:water 45:55 v/v).

In one exemplary embodiment, not intending to limit the invention in any way, the extract of Echinacea is obtained with a 1:8-1:10 ratio between Echinacea and ethanol 45%, at a suitable extraction temperature, comprised between 40 and 60° C. Normally the extraction can be protracted for 6-8 hours, then the spent residue is removed from the solution by decanting and subsequent filtration (e.g., on paper filter). In one embodiment the resulting hydroalcoholic fraction is subjected to concentration and drying by lyophilization, according to methodologies known to a technician in the field.

In one embodiment of the invention, therefore, the term "extract" corresponds to a fraction soluble in hydroalcoholic solution as above exemplified.

In the examples reported in the present description, the extract of Echinacea reported in the figures and tables as Echinacea 13C1608 is a fraction soluble in hydroalcoholic fraction, obtained from aerial parts of the plant (leaves, flowers) prepared as reported above.

That which has been set forth above with regard to the extract, meant as fraction, soluble in hydroalcoholic solution, of Echinacea, applies, mutatis mutandis, to the fraction, soluble in hydroalcoholic solution, of Centella according to the invention.

In one embodiment of the invention, the above-indicated components are in lyophilized form and are redissolved, with addition of NaCl or of another suitable salt, in the suitable concentration, in water; the mixture so obtained is heated to a temperature comprised between 30 and 70° C., preferably between 40 and 50° C., for a period of time comprised between 4 and 8 hours. The mixture so treated is then decanted and/or filtered as already indicated above, and the supernatant or the filtrate (depending on whether a decanting or a filtration has been carried out) are then lyophilized and solubilized optionally just before use, in a pharmaceutically acceptable carrier.

By way of example, the individual extracts (also meant as one or more fractions of extract as mentioned above) of Centella and Echinacea as described above, are mixed in a ratio comprised between 7:3 and 9.5:0.5 parts by weight of said extracts in lyophilized form.

In one preferred embodiment a ratio of about 8:2 or 9:1 is used, e.g., therefore 9 parts by weight of lyophilized extract of Centella asiatica and 1 part by weight of lyophilized extract of *Echinacea*, NaCl is added (q.s. to obtain a 0.9% p/V solution), and the whole is resuspended in water and treated as indicated above.

The mixture that is subjected to incubation at a temperature comprised between 30 and 70° C., preferably between 40 and 50° C., for a period of time comprised between 4 and 8 hours, can therefore be a mixture comprising 1-3% by weight of extract, lyophilized as described above, of *Centella asiatica*, 0.001-0.5% by weight of lyophilized extract of *Echinacea purpurea*, as described above, 0.5-9% of NaCl, water (preferably demineralized or deionized) q.s. to 100 ml.

Therefore, after filtration and lyophilization an extract, or more precisely a coextract is obtained, which can be mixed with one or more suitable pharmaceutically acceptable carriers for preparing the composition according to the present invention.

Such a coextract appears in form of powder highly soluble in water.

In one embodiment of the invention, the extract of *Centella asiatica* in lyophilized form obtained by extraction in 70% hydroalcoholic solution as described above, and the extract of *Centella asiatica* in lyophilized form obtained by extraction in 45% hydroalcoholic solution as described above, are mixed in a ratio *Centella:Echinacea* of about 9:1, and suspended in water in which NaCl is dissolved at a concentration comprised between 0.8 and 4%, preferably between 1.5 and 2.5%, e.g. 1.5%, 1.6%, 1.7%, 1.8% 1.9%, 2.0%, 2.1%, 2.2%, 2.3%, 2.4% or 2.5%.

Said mixture is then incubated at a temperature comprised between 30 and 70° C., preferably between 40 and 50° C., for a period of time comprised between 4 and 8 hours, and is then filtered to remove the suspended particulate (the undissolved particles), and the filtrate so obtained is lyophilized so as to obtain a coextract in form of powder easily soluble in water.

Said coextract is then dissolved in one or more pharmaceutically acceptable carriers and in order to prepare the parenteral composition of the present invention.

An example of such a coextract is that denoted in the present description and in the figures as lot 17H0246.

The term therapeutically active principle or therapeutically active component indicates that principle or that set of principles accountable for the improvement of the pathology or pathological condition treated.

According to a further embodiment, in the parenteral composition of the invention the therapeutically active principle consists in extract (or one or more fractions of extract) of *Centella asiatica* as above defined, in combination with an extract (or one or more fractions of extract) of *Echinacea purpurea* as above defined.

The composition of the invention can also be defined on the basis of its content of particular classes of substances; hereinafter, the weight concentrations of some substances relative to the weight of the composition in lyophilized form are provided. In one preferred embodiment, the parenteral composition of the invention, as above-defined, is also characterized in that said composition, in lyophilized form, is comprises:

Moreover, the parenteral composition according to the invention can also be characterized in that it comprises, in lyophilized form:
total phenols: 0.08-2% w/w, preferably 0.1-0.7%.

Again, the parenteral composition according to the invention can also be characterized in that it is comprises, in lyophilized form:
polysaccharides with MW>20000 Dalton: 1-2% w/w, preferably 1.3-1.8%.

Lastly, the parenteral composition according to the invention can also be characterized in that it comprises, in lyophilized form:
total tannins: 0.002-1% w/w.

Therefore, object of the invention is a parenteral composition comprising, when in lyophilized form, 0.08-2.0% w/w of total phenols, 0.002-1% w/w of total tannins, 1%-2% w/w of polysaccharides with a molecular weight above 20000 Da, and at least one pharmaceutically acceptable carrier, wherein said phenols, tannins; polysaccharides; are derived from *Centella asiatica* and *Echinacea purpurea*.

For the purposes of the present description, by "derived from" it is meant directly derived, therefore "extracts (or one or more fractions) from" or "comprised in extracts (or one or more fractions) of".

According to the present description, by "pharmaceutically acceptable carrier" it is meant a carrier commonly used in pharmaceutics for the preparing of injectable solutions.

In any embodiment of the invention, the extracts used may be the above-indicated ones or reworkings of the same (e.g., coextracts as described above).

In one embodiment of the invention the composition of the invention could be constituted by an extract (or one or more fractions of extract like, e.g., any one of those described herein) of *Centella asiatica*, an extract (or one or more fractions of extract such as, e.g., any one of those described herein) of *Echinacea purpurea*, and at least one pharmaceutically acceptable carrier, wherein the aforesaid extracts are according to any one of the embodiments described above. In the formulation of the composition of the invention, the therapeutically active principle as defined herein could be provided in lyophilized form, with the carrier apart, to be resuspended before use, or could be provided already dissolved into the suitable carrier.

All uses reported in the present description also apply to the embodiment defined by classes of substances, defined hereinabove.

In the formulation of the composition in any one of the embodiments according to the present description, the technician skilled in the field could conveniently select the carriers and/or the excipients among those commonly known in the state of the art.

Within the scope of the present description and in the carrying out of the invention, the term "pharmaceutically acceptable carriers" is meant in a broad sense and includes solvents, emulsifiers, buffering agents, pH correctors, antioxidants, preservatives, osmotic agents.

Besides water, for injectable preparations there could be used buffers selected, e.g., from citric, phosphoric and acetic acid and their sodium salts; pH correctors such as hydrochloric acid and sodium hydroxide, isotonic agents such as sodium chloride, sugars such as, e.g., glucose, mannitol, dextrose; and, in case, antioxidants which could be selected, e.g., from sodium bisulfite, sodium metabisulfite or sodium salts of ethylenediamine tetraacetic acid.

The use of preservatives such as benzalkonium chloride, benzethonium chloride, methyl p-hydroxybenzoate, benzyl alcohol, could be resorted to.

Emulsifiers such as, e.g., lecithins or ethoxylated derivatives of fatty acids, could be used.

For exemplary purposes, not meant as a limitation of the invention, in the implementation of the composition according to the present description, the solvents can be selected from one or more of: water, polyvinylpyrrolidone, buffered and non-buffered isotonic solutions; the emulsifiers can be selected from lecithins, ethoxylated derivatives of fatty acids; the buffering agents from citric acid and its sodium salts, phosphoric acid and its sodium salts, acetic acid and its sodium salts; the pH correctors from hydrochloric acid and sodium hydroxide; the antioxidants from sodium bisulfite, sodium metabisulfite, ethylenediamine tetraacetic acid and its sodium salts; the preservatives from benzyl alcohol, methyl p-hydroxybenzoate, benzalkonium chloride, benzethonium chloride, and the osmotic agents from sodium chloride, sugars, mannitol, dextrose, glucose.

The techniques for obtaining these sterile preparations are those commonly used in the state of the art. After having prepared a solution of extracts and excipients resorting to use of temperature to foster solubilization, the solution so obtained can be sterilized by sterilizing filtration, or by resorting to steam sterilization. In some cases, gamma ray use can be resorted to for terminal sterilization.

As described herein and as demonstrated by the examples, the parenteral composition according to any one of the embodiments set out in the present description and in the claims is suitable to be used as medicament.

In particular, the parenteral composition according to any one of the embodiments set out in the present description and in the claims is particularly suitable to be used in the treatment of disorders affecting articular cartilage in mammals.

In an exemplary and non-limiting form, said disorders affecting articular cartilage are selected from arthritis, osteoarthritis, inflammation of the joints, cartilage damage caused by trauma, degeneration of spinal discs, rheumatoid arthritis.

The parenteral composition according to any one of the embodiments set out in the present description and in the claims could be used for treating mammals in general, and therefore it will be a veterinary composition, or could be used for treating human patients, and therefore it will be a pharmaceutical composition or medical device according to current regulations.

Object of the present invention is also a therapeutic method for treating disorders affecting articular cartilage as above described, wherein the composition is administered to the patient by infiltration/injection in the zone of interest, and therefore by articular infiltration/injection. The patient, as already defined above, exhibits disorders affecting articular cartilage, may be a human being or even an animal, e.g. a mammal.

Any embodiment described above applies to the therapeutic treatment of the invention.

Object of the invention is also a process for preparing the composition according to any one of the embodiments described, wherein the therapeutically active principles as defined above, in dried form, preferably in lyophilized form, are mixed and subjected to a further step of extraction with NaCl and water, then decanted or filtered, lyophilized and resuspended with the carrier as above-defined.

Any process commonly known to the technician in the field could be used for preparing the composition according to the invention. According to an embodiment to be understood as merely exemplary and non-limiting, the process for preparing the composition of the invention can be carried out as follows 1. The extracts obtained from hydroalcoholic extraction, lyophilized, are solubilized in water with 0.8-4% NaCl, heating the mixture at a temperature comprised between 30 and 80° C., preferably between 30 and 70° C., 40 and 50° C. for a period of time comprised between 4 and 8 hours in order to foster extract solubilization.

2. The mixture obtained at the preceding point, after cooling, is filtered to eliminate any undissolved particles of extract, and is then dried, preferably by lyophilization, and resuspended in a suitable pharmaceutically acceptable carrier.

3. At this stage, oily substances and emulsifiers may be added if necessary, if surface-activated systems are to be obtained.

4. The mixture of extracts (or of fractions of extracts, like, e.g., any one of those described herein) is additioned with the other excipients soluble in water, such as buffers, isotonic agents.

5. The pH of the prepared solution is measured and suitably corrected if necessary.

6. The solution so obtained can be sterilized by sterilizing filtration or moist heat (steam) in autoclave.

Therefore, object of the invention is also a process for preparing the parenteral composition as defined above and as defined in the claims, wherein a) *Centella asiatica* leaves are subjected to one or more steps of extraction with hydroalcoholic mixtures, and the extract (or fraction/s of extract such as, e.g., any one of those described herein) so obtained is subjected to lyophilization;

b) *Echinacea purpurea* aerial parts are subjected to one or more steps of extraction with hydroalcoholic mixtures, and the extract (or fraction/s of extract, like, e.g., any one of those described herein) so obtained is subjected to lyophilization;

c) the lyophilized extracts obtained in a) and b) in any order are mixed in a ratio extract (or fraction/s of extract like, e.g., any one of those described herein) of *Centella asiatica*: extract (or fraction/s of extract, like, e.g., any one of those described herein) of *Echinacea purpurea* comprised between 7:3 and 0.5:9.5;

d) the extracts (or fractions of extract, such as, e.g., any one of those described herein) so mixed are resuspended in water additioned with 0.8-4% sodium chloride;

e) the mixture so obtained is brought to a temperature comprised between 30 and 70° C. for a time comprised between 4-8 hours and subsequently subjected to filtering or decanting;

f) the filtrate or the supernatant obtained in e) are lyophilized;

g) the lyophilizate obtained in f) is resuspended in one or more pharmaceutically acceptable carriers.

According to the invention, said extract at a) can be a fraction of extract soluble in a hydroalcoholic solution, wherein alcohol is from 65% to 75% v/v, a fraction of extract not soluble in EtOH 90-96% v/v and soluble in EtOH 10-20% v/v or a mixture thereof, as described above.

Furthermore, said extract in b) could be a fraction soluble in a hydroalcoholic solution, wherein said alcohol is from 40% to 50% v/v.

Object of the invention is also a composition obtainable by the above-described process, for all uses and in all forms provided in the present description for the parenteral composition of the invention.

The individual extracts (or fractions like, e.g., any one of those described herein) at points a) and b) can be prepared according to any one of the embodiments exemplified in the present description and in any other suitable conventional way known to the technician in the field.

The process as described above allows to prepare a parenteral composition comprising 0.08-2.0% w/w of total phenols, 0.002-1 w/w of total tannins, 1%-2% w/w of polysaccharides with a molecular weight above 20000 Da; and at least one pharmaceutically acceptable carrier, wherein said phenols, tannins, polysaccharides, are derived from *Centella asiatica* and *Echinacea purpurea*, according to the present description.

Illustrative examples of some embodiments of the invention follow.

Said examples are in no way to be understood as a limitation of the embodiments of the invention, rather having only the purpose of illustrating possible compositions implementable according to the teachings described herein, having the therapeutic features described.

COMPOSITION EXAMPLES

Composition 1
Lyophilized coextract of *Centella-Echinacea* (9:1)—NaCl*10 mg
Water for injectable preparations (f.i.p.) q.s. to 1 ml
Composition 2
Lyophilized coextract of *Centella-Echinacea* (8:2)—NaCl*10 mg
Water f.i.p. q.s. to 1 ml
Composition 3
Lyophilized coextract of *Centella-Echinacea* (9:1)—NaCl*30 mg
Tetrasodium salt of ethylenediamine tetraacetic acid 1 mg
Sodium hydroxide 0.1 mg
Benzalkonium chloride 0.2 mg
Composition 4
Lyophilized coextract of *Centella-Echinacea* (8:2)—NaCl*30 mg
Tetrasodium salt of ethylenediamine tetraacetic acid 1 mg
Sodium hydroxide 0.1 mg
Benzalkonium chloride 0.2 mg
Composition 5
Lyophilized coextract of *Centella-Echinacea* (9:1)—NaCl*50 mg
Acetic acid 1 mg
Sodium acetate 2 mg
Water f.i.p. q.s. to 1 ml
Composition 6
Lyophilized coextract of *Centella-Echinacea* (8:2)—NaCl*50 mg
Acetic acid 1 mg
Sodium acetate 2 mg
Water f.i.p. q.s. to 1 ml
Composition 7
Lyophilized coextract of *Centella-Echinacea* (9:1)—NaCl*7 mg
Monobasic sodium phosphate 1 mg
Bibasic sodium phosphate 2 mg
Water f.i.p. q.s. to 1 ml
Composition 8
Lyophilized coextract of *Centella-Echinacea* (8:2)—NaCl*7 mg
Monobasic sodium phosphate 1 mg
Bibasic sodium phosphate 2 mg
Water f.i.p. q.s. to 1 ml
Composition 9
Lyophilized coextract of *Centella-Echinacea* (9:1)—NaCl*70 mg
Benzalkonium chloride 1 mg
Water f.i.p. q.s. to 1 ml
Composition 10
Lyophilized coextract of *Centella-Echinacea* (8:2)—NaCl*70 mg
Benzalkonium chloride 1 mg
Water f.i.p. q.s. to 1 ml
*NaCl q.s. to prepare an isotonic solution.

Composition 11
Lyophilized extract of *Centella* 1 mg
Lyophilized extract of *Echinacea* 0.1 mg
NaCl 0.009 mg
Water f.i.p. q.s. to 1 ml
Composition 12
Lyophilized extract of *Centella* 25 mg
Lyophilized extract of *Echinacea* 3 mg
NaCl 0.018 mg
Water f.i.p. q.s. to 1 ml
Composition 13
Lyophilized extract of *Centella* 50 mg
Lyophilized extract of *Echinacea* 7 mg
NaCl 0.009 mg
Water f.i.p. q.s. to 1 ml The coextract according to the above examples is obtained from the extract of *Centella asiatica* in lyophilized form obtained by extraction in 70% hydroalcoholic solution as described above, and the extract of *Centella asiatica* in lyophilized form obtained by extraction in 45% hydroalcoholic solution as described above, are mixed in a ratio *Centella:Echinacea* of about 8:2 or 9:1, and suspended in water wherein NaCl is dissolved at a concentration comprised between 0.8 and 4%, preferably between 1.5 and 2.5%, e.g. 1.5%, 1.6%, 1.7%, 1.8%, 1.9%, 2.0%, 2.1%, 2.2%, 2.3%, 2.4% or 2.5%.

Said mixture is then incubated at a temperature comprised between 30 and 70° C., preferably between 40 and 50° C., for a period of time comprised between 4 and 8 hours, and is then filtered to remove the suspended particulate (the undissolved particles), and the filtrate so obtained is lyophilized so as to obtain a coextract in form of powder easily soluble in water.

Said coextract is then dissolved in one or more pharmaceutically acceptable carriers and in order to prepare the parenteral composition of the present invention.

The extract of *Centella* according to the examples above can be an extract obtained by hydroalcoholic extraction. The extract can be, e.g., prepared from crumbled *Centella* leaves that are subjected to soaking in alcohol (between 65% and 75%) at about 65%, about 70%, about 75% (non-limiting example: ethanol:water 70:30 v/v). In one exemplary embodiment, the extract of *Centella* can be obtained with a 1:8 ratio between *Centella* and alcohol 70%, at a suitable extraction temperature, comprised between 40 and 60° C. Normally, the extraction can be protracted for 6-8 hours, then the spent residue is separated from the solution by decanting and subsequent filtration. The filtrate is then lyophilized and ready for use.

The extract of *Echinacea purpurea* according to the examples above can be an extract obtained by hydroalcoholic extraction. The extract can be, e.g., prepared by extraction in hydroalcoholic solution of crumbled *Echinacea* aerial parts, e.g. in a suitable hydroalcoholic solution with alcohol between 40 and 55%, e.g. at about 40%, about 45%, about 50%, about 55% (e.g., in a non-limiting manner ethanol:water 45:55 v/v). In one exemplary embodiment, it can be obtained with a 1:10 ratio between *Echinacea* and ethanol 45%, at a suitable extraction temperature, comprised between 40 and 60° C. Normally the extraction can be protracted for 6-8 hours, then the spent residue is removed from the solution by decanting and subsequent filtration. The filtrate is then lyophilized and ready for use.

In each of the above-indicated compositions, the soluble fractions in hydroalcoholic solution provided in the present description, e.g., in the ratios indicated in the examples, in the description and in the claims, can be advantageously used as extracts.

The following data were obtained by the inventors and demonstrate the effectiveness of various embodiments of the composition of the invention.

EXPERIMENTAL ASSAYS PERFORMED

Animals

Male Sprague-Dawley rats weighing about 200 grams were provided by Harlan

Company, Italy. Four animals per cage were housed in cages of the following dimensions: 26×41 cm, at the Centre for Stabulation of Laboratory Animals (Ce.S.A.L. —Centro per la Stabulazione Animali da Laboratorio) of the University of Florence under a 12h light/dark cycle, with water and food ad libitum. Rats were fed with standard diet and housed at the temperature of 23±1° C. The experimental protocol was approved by the local Committee for the control of experimenting on laboratory animals. All experiments were conducted in accordance with the European Communities Council Directives of Sep. 22, 2010 (Directive 2010/63/EU) on the handling of animals used for experimental purposes, and with the National Institute of Health Guide for the Care and Use of Laboratory Animals, having adopted the guidelines of the International Association for the Study of Pain, and in accordance with the ARRIVE guidelines. All necessary measures were undertaken to minimize suffering and reduce the number of animals used.

Monoiodine Acetate-Induced Osteoarthritis Pain Model

Damage to the joint was induced by an individual intraarticular administration, in the paw of a pre-anesthetized rat, of 2 mg of sodium monoacetate (MIA) (volume: 25 µl) according to what described by Guingamp et al., Arthritis Rheum., 40:1670-1679, 1997.

The use of said dosage is additionally based on experiments conducted in the Inventors' laboratory, from which it emerged that 0.5- and 1-mg dosages induce a hyperalgesia disappearing within 2 weeks, whereas 4-mg dosages cause an inflammatory state lasting beyond the first week. As reported by Janusz et al., Osteoarthritis Cartilage, 9: 751-760, 2002 and Fernihoughetal., Pain 112:83-93,2004, the 2 mg dose induces chondrocytes death and marked hyperalgesia and allodynia. MIA is injected into the joint after having flexed the paw so as to form a 90°-degree angle using a 26Gx3/8 needle. Control rats received an intraarticular injection of physiological solution (25 µl).

Substances Preparation and Administration

The experiments described below were performed by injecting into the joint 20 µl of control (physiological solution);
extract of lyophilized *Echinacea purpurea*, fraction soluble in hydroalcoholic solution 40-50%, denoted in the figures as 13C1608:2-10-20 mg/ml in PBS (phosphate buffered saline);
extract of lyophilized *Centella asiatica*, fraction soluble in hydroalcoholic solution 65-75%, denoted in the figures as 14G1862:0.2-1-2 mg/ml in PBS;
bovine synovial fluid: as is;
Hyalgan (Low-molecular weight Hyaluronic acid sodium salt (MW ~500-730 kDa)):as is;
Jonexa (mixture comprised of a hylastan gel, i.e. a hyaluronic acid crosslinked with divinyl sulfone, and a sodium hyaluronate liquid in the gel-liquid ratio of 80:20): as is;
extract of *Centella asiatica* fraction soluble in hydroalcoholic solution 65-75%, denoted in the figures as 14G1862: 2 mg/ml in PBS
extract of lyophilized *Centella asiatica*, fraction soluble in hydroalcoholic solution, denoted in the figures as ABO-AR-2016-391: 2 mg/ml in PBS;
extract of lyophilized *Centella asiatica*, fraction soluble in hydroalcoholic solution, corresponding to the permeate of fraction ABO-AR-2016-391 after filtration, denoted in the figures as ABO-AR-2016-392:2 mg/ml in PBS;
extract of lyophilized *Centella asiatica*, fraction soluble in hydroalcoholic solution, corresponding to the retentate of fraction ABO-AR-2016-391 after filtration, denoted in the figures as ABO-AR-2016-393:2 mg/ml in PBS;
Triamcinolone acetonide: 100 µg/20 ml
MIX (coextract) *Centella+Echinacea* lot 17H0246, as described above: 11 mg/ml in water f.p.i.

The extracts, also meant as specific fractions obtainable from the extraction process, of *Echinacea* and *Centella*, were prepared by hydroalcoholic extraction as described above in the detailed part of the invention and in the examples below.

Injected material: 20 µL of each sample assayed were injected into rat tibiotarsal joint (using a 26Gx3/8 needle) at day 7 from damage induction by MIA.

Behavioral evaluations by Paw pressure, Von Frey, Incapacitance Beam balance, Rotarod and Animex tests, and histological analyses of articular and periarticular tissue were performed on day 14,30 and 60 from the start of the experiment.

Substances Solubilization and Administration

The mixture of plant extracts was solubilized in accordance with the following protocol: 5.5 g of lyophilized mixture were introduced in a beaker containing 450 g of water and left under stirring 15 min; thereafter, the weight of the liquid was brought to 500 g. For each injection, 30 g of solution were collected and filtered in sequence with 0.45-µ, and 0.22-µm filters. For each filtering, the first 3-4 g of solution were discarded. 20 µL of mixture were injected into the tibiotarsal joint of the rat (using a 26Gx3/8 needle) after having flexed its paw so as to form a 90°-degree angle, at day 8 from articular (joint) damage induction by MIA. For the other substances as well 20 µL of solution were injected (Hyalgan 10 mg/ml; triamcinolone acetonide 100 µg/20m1).

Paw Pressure Test

An analgesimeter (Ugo Basile, Varese, Italy) was used. A pressure increasing at a constant rate (32 g/s) was applied on the hind paw of the animal by a blunt conical element. The nociceptive threshold of the rat was expressed as that force to which the animal reacts by withdrawing the paw or vocalizing (Leighton et al., 1988).

Von Frey test

The animals were placed in a 20 cm×20 cm×15 cm Plexiglas cage whose floor is constituted by a metal grid and let habituate for 15 minutes. An electronic Von Frey apparatus (Ugo Basile, Italy) mounting a flexible metal probe, by which the volar face of the fore paw of the rat was stimulated, was placed under the metal grid. The pressure exerted increased progressively up to a maximum of 50 g, with an accuracy of 0.2 g. The sensitivity threshold of the paw was defined as the minimum pressure required to obtain a clear and immediate paw withdrawal reflex. Locomotion-associated voluntary movements were not considered as response. The stimulus was applied five times on each of the fore paws, and each value reported as sensitivity threshold is the mean of 10 consecutive measurements (Sakurai et al. Pain 147: 165-174, 2009).

Incapacitance Test

The test is based on the evaluation of the pressure exerted by a rat under conditions of normal posture on each of the hind legs (Hay et al. Neurosci. 78:843-850, 1997). Rats were placed into a small plexiglass box, their hind legs positioned onto two transducers recording the weight the rat distributes on each of the two paws. In case a neuropathy or an inflammation has been induced on one paw, the rat will exert less weight on said paw, compared to the other one.

Beam-Balance Test

A 1-meter-long wooden beam having a 1 cm-square section was placed at a height of about 40 cm. A 15 cm×15 cm×8 cm-sized black plastics box was secured onto the end portion of the beam. The animal was placed on the beam, and its motor abilities were observed, assigning an increasing score, 0 to 4, depending on the relevance of motor deficits (0, correct gait; 1, clings with the four paws; 2 slips with one paw; 3 slips with two paws; 4, falls in a time <60 s) (Song et al., 2006).

Animex

The instrument enables to record the spontaneous activity of the animals through use of electromagnetic fields and resonance circuits. The animal-containing cage is placed above the instrument; the animals, by shifting from one side to the other of the cage, modify the magnetic fields generated by the apparatus on its surface. Variations are recorded by a number counter.

Histology

Tissue samples were fixed in 4% formalin in phosphate buffer for 24 hours. Subsequently, samples were decalcified for 28 days in a suitable decalcifying solution (1.6M formic acid, 0.76M sodium formate). At the end of the decalcification, the samples were dehydrated by passages in alcohol with increasing titer, and then included in paraffin. From samples thus processed, 7 μm-thick sections were obtained which were stained by Hematoxylin-Eosin.

The samples were observed under transmitted light optical microscope to assess the morphological parameters subject of analysis:

Inflammatory infiltrate
Synovial hyperplasia
Fibrin deposition in the joint space
Synovial vascularization
Cartilage erosion
Bone erosion
Joint space width Every morphological parameter was evaluated by a specially provided score (0:absent, 1:scarce, 2:moderate, 3:serious). The evaluation was performed by three separate operators, in blind relative to the origin of the slides. A fourth operator collected data and obtained the final means. For each joint, at least three slides, and for each group at least 6 animals were evaluated. Results are expressed as mean±standard error.

Statistical Analysis

All experimental results are expressed as mean±S.E.M. A one-way analysis of variance (ANOVA) was conducted, followed by Bonferroni test to check significance between two means. Variance analysis and Bonferroni test were performed with the statistical program Origin Pro 9.1. Significant values of P<0.05 or P<0.01 were considered.

Results

Evaluation of *Centella+Echinacea* Coextract (Lot 17H0246), and Hyalgan, Jonexa, Triamcinolone Acetonide Samples' Effectiveness Object of the present research was to evaluate the antihyperalgesic and antiallodynic effectiveness of a mixture constituted by the abovementioned extracts in form of coextract according to the present description (lot17H0246) in the same pain model. Moreover, an effectiveness comparison was carried out between the aforesaid mixture and reference substances that are commonly used intraarticularly in clinical practice for treating joint pain, and specifically the hyaluronic acid preparations Jonexa and Hyalgan and the corticosteroid triamcinolone acetonide. Histological evaluations followed the behavioral evaluations performed at day 14, 30 and 60. The treatment groups:

vehicle+vehicle
MIA+vehicle
MIA+*Centella/Echinacea* mixture lot 17H0246 (20 microL)
MIA+Hyalgan (20 microL)
MIA+Jonexa (20 microL)
MIA+triamcinolone acetonide (100 microg/20 microL)

The osteoarthritis (OA) model used in this study was made by single i.a. (intraarticular) administration of MIA (2 mg/25 μl). At +8 days from damage with the algogenic agent, when the OA pathology has already onset, 20 μl of each sample (MIX (coextract) lot 17H0246; Hyalgan, 10 mg/ml; Jonexa; triamcinolone acetonide) were administered intraarticularly. Behavioral evaluations were performed at +14, +30 and +60 days from start of experiment, i.e. from MIA injection, leading to the same timings also for histological evaluations on the rat joint. The tests performed enabled to evaluate the antiperalgesic action (Paw pressure test) of the samples, the effect they have on animal posture and on the weight burdening the contralateral paw with respect to the ipsilateral one (Incapacitance test), the coordination and the motor capacity (Beam balance test) and the spontaneous activity (Animex test).

In Table 1, the antiperalgesic effect of substances, measured through a painful mechanical stimulus at +14, +30 and +60 days from damage induction, is reported. I.a. injection of MIA reduces in a statistically significant manner the algic threshold of the ipsilateral paw of the rat with respect to the control group (vehicle+vehicle) until day 60; the peak of pain reaction is recorded at 2 weeks from damage (Table 1). The single i.a. injection of the mixture of plant extracts (lot 17H0246) proves effective in reducing articular pain, starting from day 7 from its administration (Day 14 from damage with MIA). Said effect increases, culminating at day 30 with the reversal of algic conditions, as the values recorded on the ipsilateral paw are comparable to those recorded in the control group. The effect is maintained such even at day 60. Hyalgan proves to be active at day 14 and 30, though showing an effectiveness lower than the plant mixture and without culminating with the reversal of the painful condition. Jonexa proves to be active solely at day 30, whereas triamcinolone acetonide significantly reduces the articular pain reaction at all timings, however exhibiting a lesser antiperalgesic effectiveness compared to the plant mixture (Table 1).

TABLE 1

Evaluation of pain relief effects given by intraarticular injection of the samples
Table 1. Paw pressure test
Weight (g)

| Treatment | Day 14 | | Day 30 | | Day 60 | |
|---|---|---|---|---|---|---|
| | ipsilateral | contralateral | ipsilateral | contralateral | ipsilateral | contralateral |
| vehicle + vehicle | 66.7 ± 1.7 | 68.3 ± 1.7 | 67.3 ± 0.9 | 66.4 ± 1.5 | 65.3 ± 0.8 | 66.2 ± 0.8 |
| MIA + vehicle | 41.7 ± 1.7** | 61.7 ± 1.7 | 49.3 ± 1.7** | 69.2 ± 0.8 | 55.5 ± 1.4* | 66.7 ± 1.7 |
| MIA + MIX (coextract) Centella + Echinacea lot 17H0246 | 57.2 ± 1.1^^ | 65.6 ± 1.0 | 65.0 ± 1.5^^ | 70.0 ± 1.4 | 65.0 ± 1.4^^ | 67.5 ± 0.8 |
| MIA + hyalgan | 52.6 ± 0.9^^ | 62.8 ± 1.7 | 58.3 ± 0.8^ | 68.4 ± 1.4 | 59.2 ± 1.6 | 63.7 ± 1.6 |
| MIA + jonexa | 46.7 ± 1.5 | 66.7 ± 0.8 | 56.1 ± 0.5^ | 66.7 ± 0.8 | 58.4 ± 2.0 | 66.8 ± 0.9 |
| MIA + triamcinolone acetonide | 51.9 ± 1.3^^ | 64.5 ± 0.9 | 57.4 ± 0.4^ | 68.4 ± 1.6 | 63.0 ± 1.5^ | 64.9 ± 2.1 |

Monoarthritis was induced by injection of 2 mg/25 μL of monoiodoacetate (MIA, Sigma-Aldrich) in the tibiotarsal joint. At day 8 after MIA injection, 20 μL of the mixture of extracts of Centella and Echinacea, Hyalgan, Jonexa (as it) and triamcinolone acetonide (100 μg) were injected in rat tibiotarsal joint.
**P < 0.01 vs vehicle + vehicle;
^P < 0.05 and
^^P < 0.01 vs MIA + vehicle The incapacitance test shows a greater effectiveness of the treatment with the mixture, compared to other substances, in reducing the postural alteration induced by MIA administration, which leads to the animal burdening to a greater extent weight on the contralateral paw, with respect to the ipsilateral one (Table 2). The MIX (coextract) Centella+Echinacea lot 17H0246 in fact redresses the balance of the aforesaid alteration at all timings considered (14, 30 and 60 days), reaching the control values at two months from start of experiment. Triamcinolone acetonide reduces, it also in a statistically significant manner, MIA-induced alteration at all timings considered, though with a lesser effectiveness with respect to the MIX (coextract) Centella+Echinacea lot 17H0246. As shown to the Paw pressure test, Hyalgan is active at days 14 and 30, then losing effectiveness, whereas Jonexa reaches statistical significance only at day 30 (Table 2).

TABLE 2

Table 2. Incapacitance test
Δ Weight (g)
Score difference
(contralateral - ipsilateral paw)

| Treatments | Day 14 | Day 30 | Day 60 |
|---|---|---|---|
| vehicle + vehicle | −0.8 ± 1.2 | 6.7 ± 4.9 | 3.6 ± 7.8 |
| MIA + vehicle | 73.0 ± 13.0** | 49.8 ± 2.8** | 36.2 ± 3.2** |
| MIA + MIX (coextract) Centella + Echinacea lot 17H0246 | 30.4 ± 1.9^^ | 16.7 ± 6.4^^ | 3.4 ± 2.1^^ |
| MIA + hyalgan | 42.8 ± 7.5^^ | 23.8 ± 2.5^^ | 28.9 ± 5.8 |
| MIA + jonexa | 56.9 ± 18.1 | 32.0 ± 6.3^ | 32.4 ± 6.1 |
| MIA + triamcinolone acetonide | 45.7 ± 3.9^^ | 25.4 ± 4.3^^ | 20.9 ± 5.4^ |

Monoarthritis was induced by injection of 2 mg/25 μL of monoiodine acetate (MIA, Sigma-Aldrich) in the tibiotarsal joint. At day 8 after MIA injection, 20 μL of the mixture Centella + Echinacea, Hyalgan, Jonexa and triamcinolone acetonide (100 μg) were injected in rat tibiotarsal joint.
**P < 0.01 vs vehicle + vehicle;
^P < 0.05 and ^^P < 0.01 vs MIA + vehicle The Beam balance test (Table 3) was performed with the purpose of evaluating the motor abilities of the animal when placed on a wooden beam raised off the ground. The score assigned to each group is comprised between 0 and 4 (0 for a correct gait, 1 if clinging with the four paws, 2 if slipping with one paw, 3 if slipping with two paws, 4 if falling in a time <60 s). MIA-treated animals (MIA+vehicle) place with great difficulty the ipsilateral paw on the beam, and for this reason slip when walking thereon. Repeating this experiment at various times from MIA administration highlights how the effect of said agent causes a motor impairment which is maximum in the first 14 days, an effect later tending to reduce spontaneously in the course of time. The single administration of MIX (coextract) Centella+Echinacea lot 17H0246 causes the score assigned to these animals to be halved with respect to the MIA+vehicle group at all times considered, even though statistical significance is reached solely at day 14, as well as for Hyalgan and triamcinolone acetonide. Jonexa is ineffective (Table 3).

TABLE 3

Table 3. Beam balance test
Limit: from normal (0) to pathological (4) value

| Treatments | Day 14 | Day 30 | Day 60 |
|---|---|---|---|
| vehicle + vehicle | 0.3 ± 0.2 | 0.2 ± 0.3 | 0.2 ± 0.3 |
| MIA + vehicle | 3.2 ± 0.4** | 1.5 ± 0.2* | 1.3 ± 0.2* |
| MIA + MIX (coextract) Centella + Echinacea lot 17H0246 | 1.3 ± 0.2^^ | 0.5 ± 0.2 | 0.7 ± 0.2 |
| MIA + hyalgan | 1.5 ± 0.3^^ | 1.0 ± 0.1 | 1.0 ± 0.2 |
| MIA + jonexa | 2.3 ± 0.4 | 1.0 ± 0.2 | 1.0 ± 0.210 |
| MIA + triamcinolone acetonide | 1.8 ± 0.2^ | 1.3 ± 0.2 | 0.8 ± 0.2 |

Monoarthritis was induced by injection of 2 mg/25 μL of monoiodine acetate (MIA, Sigma-Aldrich) into the tibiotarsal joint. At day 8 after MIA injection, 20 μL of the mixture Centella + Echinacea, Hyalgan, Jonexa and triamcinolone acetonide (100 μg) were injected into rat tibiotarsal joint.
**P < 0.01 vs vehicle + vehicle;
^P < 0.05 and ^^P < 0.01 vs MIA + vehicle Finally, by Animex test, the spontaneous mobility of the animal was evaluated (Table 4). In this case, the number of spontaneous movements of the rat, once placed in a Plexiglas cage, was recorded. The results obtained are analogous to those recorded in preceding tests, the reduction of spontaneous movements of the animal that is recorded in the MIA+vehicle group is significantly reduced by the treatment with MIX (coextract) *Centella+Echinacea* lot 17H0246 at all timings considered. Even though this also occurs with triamcinolone acetonide, its effectiveness is lower than that of the plant mixture. Hyalgan reaches statistical significance at days 14 and 30, whereas Jonexa only at day 30 (Table 4). In short, the i.a. treatment with the mixture of plant extracts (MIX (coextracts) *Centella+Echinacea* lot 17H0246) proves to be more effective in reducing articular pain following MIA administration in the experimental animal, compared to the injection of Hyalgan, Jonexa and triamcinolone acetonide. Besides the greater effectiveness, the antiperalgesic profile of this treatment protracts over time until complete reversal of the algic pathology.

TABLE 4

Table 4. Animex test
Number of movements

| Treatments | Day 14 | Day 30 | Day 60 |
|---|---|---|---|
| vehicle + vehicle | 736.4 ± 45.9 | 698.3 ± 35.9 | 720.6 ± 52.3 |
| MIA + vehicle | 298.7 ± 60.4** | 455.0 ± 26.7** | 510.7 ± 42.0* |
| MIA + MIX (COEXTRACT) *Centella + Echinacea* lot 17H0246 | 547.3 ± 50.8^^ | 664.3 ± 39.8^^ | 704.9 ± 53.1^ |
| MIA + hyalgan | 517.0 ± 35.6^^ | 549.6 ± 45.1^ | 599.9 ± 54.3 |
| MIA + jonexa | 358.1 ± 42.8 | 568.1 ± 38.7^ | 604.3 ± 39.7 |
| MIA + triamcinolone acetonide | 487.3 ± 57.3^ | 583.3 ± 45.2^ | 688.9 ± 54.2^ |

Monoarthritis was induced by injection of 2 mg/25 μL of monoiodine acetate (MIA, Sigma-Aldrich) into the tibiotarsal joint. At day 8 after MIA injection, 20 μL of the mixture *Centella + Echinacea*, Hyalgan, Jonexa and triamcinolone acetonide (100 μg) were injected into rat tibiotarsal joint.
**$P < 0.01$ vs vehicle + vehicle;
^$P < 0.05$ and ^^$P < 0.01$ vs MIA + vehicle Histological evaluations of the tibiotarsal joint of animals treated with coextract *Centella+Echinacea* (lot 17H0246), Hyalgan, Jonexa, triamcinolone acetonide MIA: overall, in analyzed animals there are observed a reduction of articular space not dependent on observation time, and the deposition of fibrin filaments in the joint space, increasing after 30 and 60 days from treatment. Erosion phenomena on cartilage of encrustment and subchondral bone have a time-dependent ingravescent pattern. Synovial hyperplasia and vascularization phenomena are detectable. Moreover, the presence of inflammatory infiltrate is highlighted, exhibiting a reduction after 60 days from inoculation (FIG. 18 A-G and FIG. 19).

MIA+MIX (coextract) *Centella+Echinacea* lot 17H0246: the treatment with MIX (coextract) *Centella+Echinacea* lot 17H0246 modifies the morphological parameters analyzed. As to the inflammatory infiltrate, said treatment significantly reduces it after 30 and 60 days. At synovial level, it eliminates the damage induced by treatment with MIA. The cartilage of encrustment and the subchondral bone tissue in animals treated with MIX (coextract) *Centella+Echinacea* lot 17H0246 appear erosion-free after 30 and 60 days. Fibrin deposition in the articular space is absent after 30 and 60 days; likewise, the articular space returns to values compatible with those detected in control animals (FIGS. 18 A-G and FIG. 19).

MIA+Jonexa: the treatment with Jonexa gives no significant improvement in the morphological parameters analyzed, in comparison with the group of animals treated with the sole MIA. A slight improvement on articular space width (FIG. 18 A-G and FIG. 19) is highlighted.

MIA+Hyalgan: no significant improvement is highlighted following treatment with Hyalgan. A slight improvement on articular space width (FIG. 18 A-G and FIG. 19) is highlighted.

MIA+triamcinolone acetonide: the treatment with triamcinolone acetonide is capable of eliminating the presence of inflammatory infiltrate at all timings analyzed. An analogous result is highlighted as regards the erosion phenomena affecting articular cartilage and subchondral bone. Evident effects can be highlighted on the articular space after 30 and 60 days. More moderate effects can be highlighted on hyperplastic and vascular phenomena on synovia and as regards fibrin deposition in the articular space (FIG. 18 A-G and FIG. 19).

Evaluation of effectiveness of extracts of *Echinacea* (13C1608) and *Centella* (14G1862) (fractions soluble in hydroalcoholic solution) on bovine synovial fluid 20 μL of each substance were injected into rat tibiotarsal joint when the osteoarthritic pathology has already onset (8 days after induction or articular damage caused by i.a. administration of MIA). Behavioral evaluations were conducted at day 14, 30 and 60 from damage induction. The effectiveness of extracts of *Centella* (fraction 14G1862) and *Echinacea* (fraction 13C1608) and the antihyperalgesic action of the bovine synovial fluid were evaluated by Paw Pressure test (measuring the pain threshold of the animal by a painful mechanical stimulus) and Von Frey test (measuring the pain threshold of the animal by a non-painful mechanical stimulus). The difference of weight the animal burdens on the hind legs was evaluated through Incapacitance test (the animal with a monolateral pain tends to burden more weight on the contralateral paw, compared to the ipsilateral paw).

In Table 5, the effect of the various substances on the algic perception threshold evaluated on the ipsilateral paw (Paw pressure test) is shown. The group of animals injected with MIA (MIA+vehicle) shows a reduction of the algic threshold compared to the group of control animals (vehicle+vehicle) which is maximum at day 14 from damage induction (43.7±1.7 and 64.2±1.5, respectively). This difference in the two experimental groups remains significant even at day 30 and 60, though a spontaneous decrease of the algic pathology is highlighted in the course of days. The single i.a. injection of the fraction soluble in 45% hydroalcoholic solution of *Echinacea* (20 mg/ml) proves effective in reducing articular pain starting from day 6 from its administration (day 14 from damage with MIA). The effect of complete reversal of the osteoarthritic pathology is obtained at day 60, since the values recorded on the ipsilateral paw in the control group and in the group of MIA-treated animals+fraction of *Echinacea* (20 mg/ml) are comparable. The smaller dose of fraction of *Echinacea* assayed (2 mg/ml) is not active, whereas the 10 mg/ml dose shows a significant effect solely at day 14.

The fraction soluble in 70% hydroalcoholic solution of *Centella* is effective only at the maximum dose assayed (2 mg/ml). The antihyperalgesic effect is found already from day 14 from damage with MIA and remains significant, reaching complete reversal, at day 30 and 60.

The single i.a. administration of bovine synovial fluid induces an effect of reduction of osteoarthritic symptomatology that is statistically significant at day 14; the successive evaluations do not reach said significance.

In Table 6 it is shown the antiallodynic effect in time course of the single tibiotarsal administration of the various products in animals subjected to a non-painful mechanical stimulus (Von Frey test). MIA-treated animals bear on the ipsilateral paw a weight halved with respect to the control group. The allodynic effect induced by MIA injection remains throughout the experiment (60 days), exhibiting however a greater effect after 14 days from its administration. The fractions of *Echinacea* and *Centella* exhibit a comparable pattern throughout the experiment. For both, an antiallodynic effect is recorded already at day 14; said effect gradually increases in the course of days and culminates with the reversal of algic symptomatology at day 60 from articular damage. As regards synovial fluid, the data obtained are comparable to those recorded at the Paw pressure test.

The incapacitance test shows a greater effectiveness of the fractions of *Centella* (2 mg/ml) and *Echinacea* (20 mg/ml) compared to the administration of synovial fluid. The injection of the two plant fractions entails a halving of the weight difference the animal burdens on the contralateral paw compared to the ipsilateral paw (Table 7). This effect proves to be statistically significant in in all measurements performed (14, 30 and 60 days). Both fractions, once assayed at lower doses, did not prove effective. The tests for determining motor abilities, motor coordination abilities (Beam Balance and Rotarod test, respectively) and spontaneous movement activity (Animex test) enabled to demonstrate that the animals damaged with MIA and subsequently treated with the fractions of *Echinacea* and *Centella* have retained good abilities of movement and motor coordination (data not shown).

In short, the fractions of *Echinacea* (20 mg/mL) and *Centella* (2 mg/mL) prove to be more active in reducing articular pain subsequent to MIA administration in the experimental animal, compared to the injection of synovial fluid. Specifically, the two extracts exhibit an antihyperalgesic profile that remains constant over time after their single i.a. administration

TABLE 5

Paw pressure test
Weight (g)

| Treatments | Day 14 | | Day 30 | | Day 60 | |
|---|---|---|---|---|---|---|
| | ipsilateral | contralateral | ipsilateral | contralateral | ipsilateral | contralateral |
| vehicle + vehicle | 64.2 ± 1.5 | 62.1 ± 0.9 | 65.8 ± 1.1 | 62.7 ± 1.2 | 63.4 ± 0.8 | 63.7 ± 1.5 |
| MIA + vehicle | 43.3 ± 1.7** | 65.0 ± 0.3 | 51.3 ± 1.2** | 62.5 ± 1.4 | 57.5 ± 1.4* | 65.8 ± 0.8 |
| MIA + Extract of *Echinacea*, fraction 13C1608 2 mg/ml | 46.8 ± 1.6 | 60.5 ± 1.2 | 50.6 ± 2.5 | 63.4 ± 0.7 | 61.4 ± 2.5 | 63.7 ± 1.4 |
| MIA + Extract of *Echinacea*, fraction 13C1608 10 mg/ml | 52.1 ± 0.4^ | 64.4 ± 0.9 | 49.7 ± 0.9 | 62.9 ± 0.5 | 59.8 ± 2.6 | 60.7 ± 2.8 |
| MIA + Extract of *Echinacea*, fraction 20 mg/ml | 54.2 ± 2.2^^ | 63.3 ± 0.8 | 58.3 ± 0.8^ | 61.7 ± 0.8 | 63.3 ± 1.7^ | 65.8 ± 0.8 |
| MIA + Extract of *Centella*, fraction 14G1862 0.2 mg/ml | 44.7 ± 1.6 | 66.1 ± 2.3 | 52.7 ± 0.8 | 61.6 ± 1.4 | 61.6 ± 0.7 | 64.3 ± 1.5 |
| MIA + Extract of *Centella*, fraction 14G1862 1 mg/ml | 47.6 ± 2.1 | 62.9 ± 0.9 | 52.9 ± 1.3 | 64.8 ± 2.3 | 63.4 ± 1.1 | 61.9 ± 2.5 |
| MIA + Extract of *Centella*, fraction 14G1862 2 mg/ml | 59.2 ± 3.0^^ | 64.2 ± 0.8 | 60.0 ± 1.4^^ | 63.3 ± 0.8 | 63.3 ± 1.7^ | 64.2 ± 0.8 |
| MIA + Synovial fluid | 53.3 ± 1.7^^ | 62.5 ± 1.4 | 55.8 ± 0.8 | 61.7 ± 1.7 | 59.2 ± 3.0 | 63.3 ± 0.8 |

Monoarthritis was induced by injections of 2 mg/25 μL of monoiodine acetate (MIA, Sigma-Aldrich) into the tibiotarsal joint. At day 8 after MIA injection, 20 μL of each plant fraction or compound were injected into rat tibiotarsal joint. The fractions of *Echinacea* and *Centella* were dissolved in PBS.
*$P < 0.05$ and
**$P < 0.01$ vs vehicle + vehicle;
^$P < 0.05$ and
^^$P < 0.01$ vs MIA + vehicle

TABLE 6

Von Frey test
Retraction threshold (g)

| Treatments | Day 14 ipsilateral | Day 14 contralateral | Day 30 ipsilateral | Day 30 contralateral | Day 60 ipsilateral | Day 60 contralateral |
|---|---|---|---|---|---|---|
| vehicle + vehicle | 23.7 ± 0.7 | 22.5 ± 1.4 | 25.6 ± 1.4 | 23.7 ± 2.8 | 24.5 ± 1.3 | 24.6 ± 2.1 |
| MIA + vehicle | 11.0 ± 0.3** | 22.7 ± 0.4 | 14.1 ± 1.2** | 23.8 ± 0.8 | 16.5 ± 1.0** | 23.4 ± 1.7 |
| MIA + Extract of *Echinacea*, fraction 13C1608 2 mg/ml | 12.3 ± 1.5 | 23.4 ± 0.8 | 14.9 ± 2.0 | 20.1 ± 2.3 | 18.7 ± 1.1 | 22.9 ± 0.7 |
| MIA + Extract of *Echinacea*, fraction 13C1608 10 mg/ml | 13.6 ± 2.1 | 21.6 ± 2.4 | 15.7 ± 0.8 | 25.0 ± 1.1 | 21.3 ± 0.4^ | 23.0 ± 2.3 |
| MIA + Extract of *Echinacea*, fraction 13C1608 20 mg/ml | 16.0 ± 0.8^^ | 24.0 ± 0.6 | 19.5 ± 1.7^ | 25.2 ± 0.8 | 22.4 ± 0.8^^ | 24.7 ± 0.5 |
| MIA + Extract of *Centella*, fraction 14G1862 0.2 mg/ml | 11.9 ± 0.8 | 23.7 ± 1.6 | 16.4 ± 1.5 | 23.7 ± 1.6 | 19.6 ± 2.1 | 22.6 ± 1.3 |
| MIA + Extract of *Centella*, fraction 14G1862 1 mg/ml | 12.6 ± 1.6 | 20.8 ± 0.9 | 16.7 ± 0.6 | 20.8 ± 0.9 | 18.4 ± 1.9 | 21.8 ± 0.9 |
| MIA + Extract of *Centella*, fraction 14G1862 2 mg/ml | 15.9 ± 0.5^^ | 22.8 ± 0.6 | 18.7 ± 0.9^ | 25.1 ± 0.8 | 22.3 ± 1.4^^ | 24.7 ± 1.7 |
| MIA + Synovial fluid | 14.9 ± 1.0^^ | 23.4 ± 0.3 | 18.2 ± 0.8^ | 24.1 ± 0.3 | 19.9 ± 1.1 | 24.5 ± 0.5 |

Monoarthritis was induced by injections of 2 mg/25 μL of monoiodine acetate (MIA, Sigma-Aldrich) into the tibiotarsal joint. At day 8 after MIA injection, 20 μL of each plant fraction or compound were injected into rat tibiotarsal joint. The fractions of *Echinacea* and *Centella* were dissolved in PBS.
**$P < 0.01$ vs vehicle + vehicle;
^$P < 0.05$ and
^^$P < 0.01$ vs MIA + vehicle

TABLE 7

Incapacitance test
Δ Weight (g)
(contralateral - ipsilateral paw)

| Treatments | Day 14 | Day 30 | Day 60 |
|---|---|---|---|
| vehicle + vehicle | 2.7 ± 3.8 | 10.5 ± 6.7 | −5.9 ± 4.2 |
| MIA + vehicle | 55.4 ± 1.9** | 38.9 ± 1.5** | 17.3 ± 1.4** |
| MIA + extract of *Echinacea*, fraction 13C1608 2 mg/ml | 44.9 ± 3.7 | 42.5 ± 4.6 | 13.1 ± 3.6 |
| MIA + extract of *Echinacea*, fraction 13C1608 10 mg/ml | 39.6 ± 10.9 | 31.4 ± 5.8 | 11.8 ± 3.9 |
| MIA + extract of *Echinacea*, fraction 13C1608 20 mg/ml | 29.7 ± 2.7^^ | 28.0 ± 0.9^^ | 7.3 ± 0.2^^ |

TABLE 7-continued

Incapacitance test
Δ Weight (g)
(contralateral - ipsilateral paw)

| Treatments | Day 14 | Day 30 | Day 60 |
|---|---|---|---|
| MIA + Extract of Centella, fraction 14G1862 0.2 mg/ml | 48.6 ± 9.4 | 33.6 ± 1.9 | 14.8 ± 2.4 |
| MIA + Extract of Centella, fraction 14G1862 1 mg/ml | 39.3 ± 9.8 | 35.0 ± 5.6 | 12.3 ± 3.5 |
| MIA + Extract of Centella, fraction 14G1862 2 mg/ml | 19.8 ± 7.4^^ | 12.8 ± 4.1^^ | 8.1 ± 1.2^ |
| MIA + Synovial fluid | 34.7 ± 2.0^^ | 29.4 ± 0.9^^ | 10.8 ± 0.9^ |

Monoarthritis was induced by injections of 2 mg/25 μL of monoiodine acetate (MIA, Sigma-Aldrich) into the tibiotarsal joint. At day 8 after MIA injection, 20 μL of each plant fraction or compound were injected into rat tibiotarsal joint. The fractions of Echinacea and Centella were dissolved in PBS.
**$P < 0.01$ vs vehicle + vehicle;
^$P < 0.05$ and ^^$P < 0.01$ vs MIA + vehicle Histological evaluations of the tibiotarsal joint of animals treated with extracts of Echinacea (fraction 13C1608) and Centella (fraction 14G1862), bovine synovial fluid MIA: overall, in analyzed animals there are observed a reduction of articular space not dependent on observation time, and the deposition of fibrin filaments in the articular space, increasing after 30 and 60 days from treatment. Overall, cartilage and bone tissue erosion show a time-dependent increase. Synovial hyperplasia and vascularization are present and reduce in the course of time from treatment. Moreover, the presence of a modest inflammatory infiltrate, not exhibiting time-dependent patterns, is highlighted (FIGS. 1 and 2).

MIA+Centella (14G1862)(2 mg/ml): the treatment with Centella 14G1862 overall reduces in a statistically significant manner all morphological alterations highlighted, above all at times of 30 and 60 days. Minor fibrin depositions or small foci of bone erosion remain (FIGS. 1 and 2).

MIA+Echinacea purpurea (13C1608) (20 mg/ml): the treatment with Echinacea 13C1608 overall reduces in a statistically significant manner all morphological alterations highlighted, above all at times of 30 and 60 days. Minor fibrin depositions or small foci of bone erosion remain (FIGS. 1 and 2).

MIA+Bovine synovial fluid: the treatment with bovine synovial fluid does not seem to modify morphological parameters with respect to the outline described for MIA-treated animals (FIGS. 1 and 2).

Evaluation of Effectiveness of Various Fractions Soluble in Hydroalcoholic Solution of Centella asiatica In the same animal model of MIA-induced osteoarthritis, there were evaluated the effectiveness of intraarticular administration of three fractions of Centella (ABO-AR-2016-391, ABO-AR-2016-392 and ABO-AR-2016-393) and finally with the effect generated by intraarticular treatment with triamcinolone acetonide. Behavioral evaluations were performed at 14, 30 and 60 days from damage induction, whereas intraarticular administration of the substances was performed at 8 days from MIA (when the osteoarthritic pathology has already onset).

In Table 8 the effect of the various treatments on the algic perception threshold by a painful mechanical stimulus (Paw Pressure test) is shown. The group of animals injected with MIA (MIA+vehicle) shows a statistically significant reduction of pain threshold with respect to the control group which is maximum at Day 14 from damage induction (41.5±1.9 g, and 65.0±1.6 g, respectively). This difference between the two experimental groups remains significant even at day 30, to then wane after 60 days, when a spontaneous recovery from the osteoarthritic pathology occurs (Table 8). The single i.a. injection of the fraction, soluble in EtOH 70%, of Centella (14G1862) reduces articular pain starting from day 6 from its administration (day 14 from damage with MIA). A near-complete reversal of articular algic condition is obtained at day 30, when the values recorded on the ipsilateral paw in the control group and in the group of MIA-treated animals+extract of Centella, fraction 14G1862 are comparable (65.2±0.9 g and 60.0±1.4 g, respectively). The fractions of Centella ABO-AR-2016-391 and ABO-AR-2016-392 prepared as described in the preparation example 4, below, are significantly active after 14 and 30 days, showing at day 14 a lower effectiveness compared to the treatment with extract of Centella, fraction 14G1862, as they only partially reduce MIA-induced hyperalgesia. The extract of Centella, fraction ABO-AR-2016-393, reaches statistical significance only at day 30 (58.3±1.7 g), it also showing an effectiveness comparable to that of the extract of Centella, fraction (14G1862). The effectiveness of fractions ABO-AR-2016-391 and ABO-AR-2016-392 is comparable to that induced by i.a. treatment with triamcinolone acetonide (52.8±1.1 g and 56.7±2.5 g, at days 14 and 30, respectively) (Table 8).

TABLE 8

Paw pressure test
Weight (g)

| | Day 14 | | Day 30 | | Day 60 | |
|---|---|---|---|---|---|---|
| Treatments | ipsilateral | contralateral | ipsilateral | contralateral | ipsilateral | contralateral |
| vehicle + vehicle | 65.0 ± 1.6 | 65.0 ± 2.5 | 65.2 ± 0.9 | 66.3 ± 1.3 | 62.5 ± 2.5 | 65.0 ± 0.6 |
| MIA + vehicle | 41.5 ± 1.9** | 65.0 ± 2.9 | 48.0 ± 1.8** | 65.8 ± 3.0 | 59.2 ± 0.8 | 63.3 ± 1.7 |
| MIA + Extract of Centella, fraction 14G1862 | 59.2 ± 3.0^^ | 64.2 ± 0.8 | 60.0 ± 1.4^^ | 63.3 ± 0.8 | 63.3 ± 1.7 | 64.2 ± 0.8 |

TABLE 8-continued

| | Paw pressure test Weight (g) | | | | | |
|---|---|---|---|---|---|---|
| | Day 14 | | Day 30 | | Day 60 | |
| Treatments | ipsilateral | contralateral | ipsilateral | contralateral | ipsilateral | contralateral |
| MIA + Extract of *Centella*, fraction ABO-AR-2016-391 | 50.4 ± 2.2^ | 64.4 ± 0.9 | 57.5 ± 1.4^ | 65.8 ± 0.8 | 56.7 ± 0.8 | 70.0 ± 2.9 |
| MIA + Extract of *Centella*, fraction ABO-AR-2016-392 | 51.2 ± 1.3^^ | 63.3 ± 0.8 | 56.7 ± 3.3^ | 63.4 ± 1.4 | 61.3 ± 1.3 | 65.8 ± 0.8 |
| MIA + Extract of *Centella*, fraction ABO-AR-2016-393 | 48.8 ± 2.2 | 66.1 ± 2.3 | 58.3 ± 1.7^^ | 64.2 ± 2.2 | 63.3 ± 1.7 | 72.5 ± 1.4 |
| MIA + triamcinolone acetonide | 52.8 ± 1.1 | 65.3 ± 1.0 | 56.7 ± 2.5^^ | 65.8 ± 0.5 | 61.3 ± 1.6 | 66.4 ± 0.7 |

Monoarthritis was induced by injections of 2 mg/25 µL of monoiodine acetate (MIA, Sigma-Aldrich) into the tibiotarsal joint. At day 8 after MIA injection, 20 µL of each plant fraction(2 mg/ml) or triamcinolone acetonide (100 µg) were injected into rat tibiotarsal joint. *Centella* fractions were dissolved in PBS.
\*\*P < 0.01 vs vehicle + vehicle;
^P < 0.05 and
^^P < 0.01 vs MIA + vehicle The incapacitance test shows an effectiveness greater than that of the fractions of *Centella* 14G1862, ABO-AR-2016-392 with respect to the administration of fractions ABO-AR-2016-391, ABO-AR-2016-393 and with respect to the cortisone-based drug treatment. The injection of fractions 14G1862, ABO-AR-2016-392 entails the halving of the weight difference the animal burdens on the contralateral paw with respect to the ipsilateral paw (Table 9). This effect proves to be statistically significant in measurements carried out both at 14 and at 30 days. ABO-AR-2016-391 induces a significant effect at 14 days (30.9±5.0 g) from damage with MIA, whereas the fraction ABO-AR-2016-393 reaches statistical significance at day 30 (10.6±0.8 g). The treatment with triamcinolone acetonide is active both at days 14 and 30 but, as mentioned above, with a lower effectiveness compared to the fractions of *Centella* 14G1862 and ABO-AR-2016-392 (Table 9).

TABLE 9

| | Incapacitance test Δ Weight (g) (paw contralateral - ipsilateral) | | |
|---|---|---|---|
| Treatments | Day 14 | Day 30 | Day 60 |
| vehicle + vehicle | −9.8 ± 2.5 | 3.5 ± 5.2 | 9.7 ± 5.2 |
| MIA + vehicle | 56.8 ± 7.1\*\* | 31.5 ± 1.5\*\* | 10.4 ± 2.7 |
| MIA + Extract of *Centella*, fraction 14G1862 | 19.8 ± 7.4^^ | 12.8 ± 4.1^^ | 8.1 ± 1.2 |
| MIA + Extract of *Centella*, fraction ABO-AR-2016-391 | 30.9 ± 5.0^ | 24.1 ± 3.8 | 6.3 ± 4.5 |
| MIA + Extract of *Centella*, fraction ABO-AR-2016-392 | 20.5 ± 3.1^^ | 6.3 ± 3.4^^ | −2.6 ± 8.8 |

TABLE 9-continued

| | Incapacitance test Δ Weight (g) (paw contralateral - ipsilateral) | | |
|---|---|---|---|
| Treatments | Day 14 | Day 30 | Day 60 |
| MIA + Extract of *Centella*, fraction ABO-AR-2016-393 | 41.6 ± 2.8 | 10.6 ± 0.8^^ | 5.6 ± 4.4 |
| MIA + triamcinolone acetonide | 28.7 ± 3.2^ | 15.6 ± 5.4^ | 5.6 ± 4.4 |

Monoarthritis was induced by injections of 2 mg/25 µL of monoiodine acetate (MIA, Sigma-Aldrich) into the tibiotarsal joint. At day 8 after MIA injection, 20 µL of each plant fraction (2 mg/ml) or triamcinolone acetonide (100 µg) were injected into rat tibiotarsal joint. *Centella* fractions were dissolved in PBS.
\*\*P < 0.01 vs vehicle + vehicle;
^P < 0.05 and ^^P < 0.01 vs MIA + vehicle The test of evaluation of spontaneous movement activity (Animex test) enabled to demonstrate that the animals treated with extract of *Centella* retained good abilities of movement (data not shown). In this test, the most effective extracts are those of *Centella*, fractions 14G1862 and ABO-AR-2016-392, as increasing in a statistically significant manner the number of spontaneous movements of the animal, both at 14 and at 30 days from the damage (data not shown). In short, the extracts of *Centella* that reported a greater effectiveness in reducing hyperalgesia and motor impairment subsequent to MIA administration are the fraction of *Centella* 14G1862 and the fraction ABO-AR-2016-392. Specifically, they exhibited an analgesic profile that remains constant over time after their individual i.a. administration.

Relation on Histological Evaluations of the Tibiotarsal Joint of Animals Treated with Various Fractions of *Centella* and with Triamcinolone Acetonide MIA: Overall, in analyzed animals there are observed a reduction of articular space not dependent on observation time, and the deposition of fibrin filaments in the articular space, increasing after 30 and 60 days from treatment. Overall, cartilage and bone tissue erosion show a time-dependent increase. Synovial hyperplasia and vascularization are present and reduce in the course of time from the treatment. Moreover, the presence of a modest inflammatory infiltrate, not exhibiting time-dependent patterns, is highlighted (FIGS. 3 and 4).

MIA+*Centella* 14G1862: the treatment with *Centella* 14G1862 overall reduces in a statistically significant manner all morphological alterations highlighted, above all at 30 and 60 days times. Minor fibrin depositions or small foci of bone erosion remain (FIGS. 3 and 4).

Figure 5:
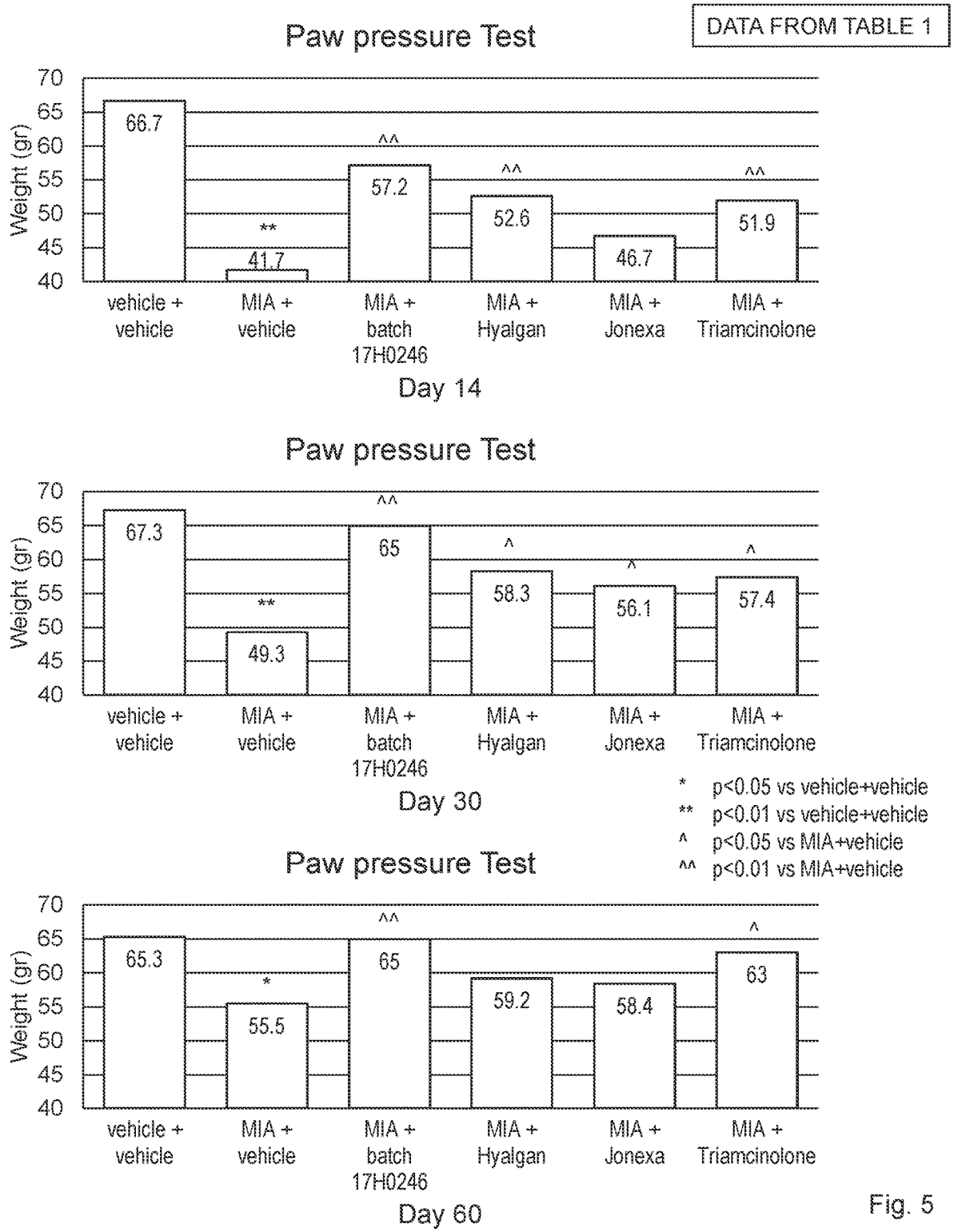
Figure 6:
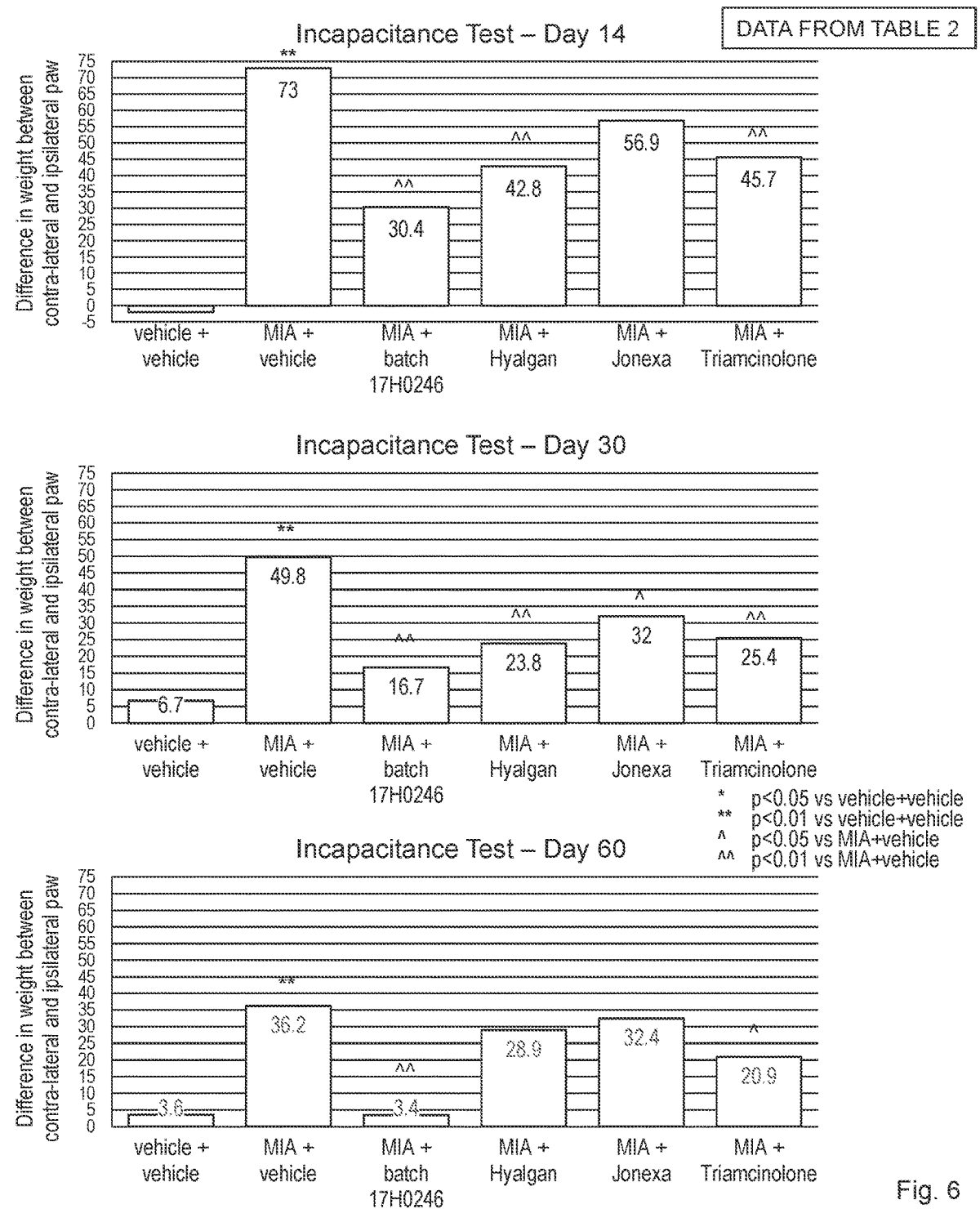
Figure 7:
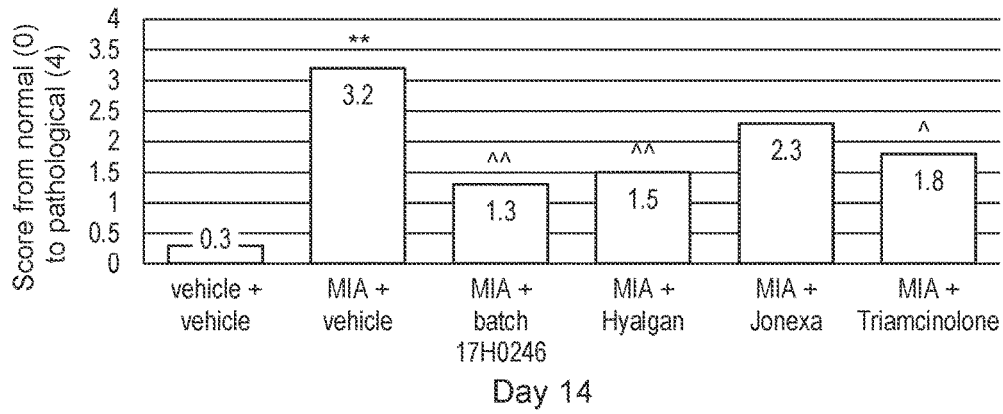
Figure 7:
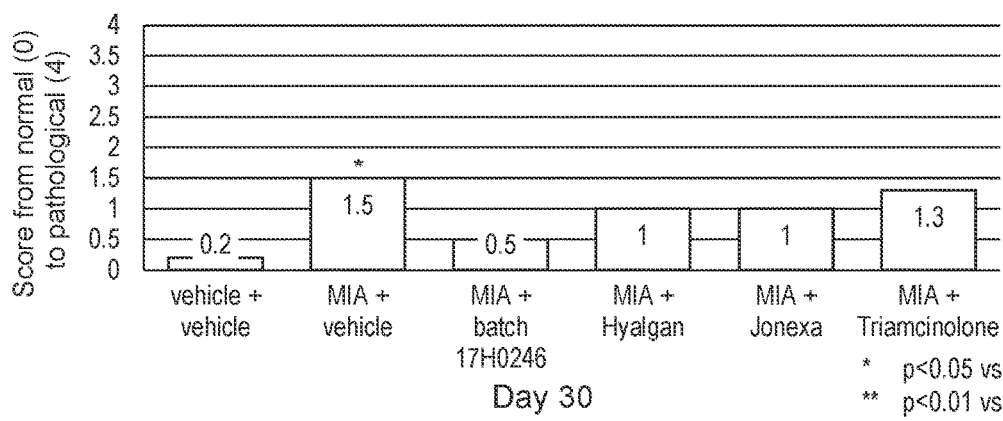
Figure 7:
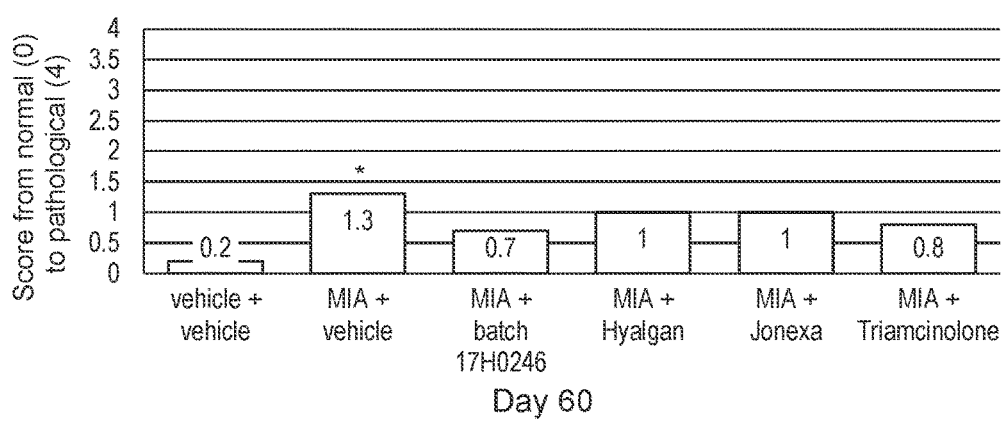
Figure 8:
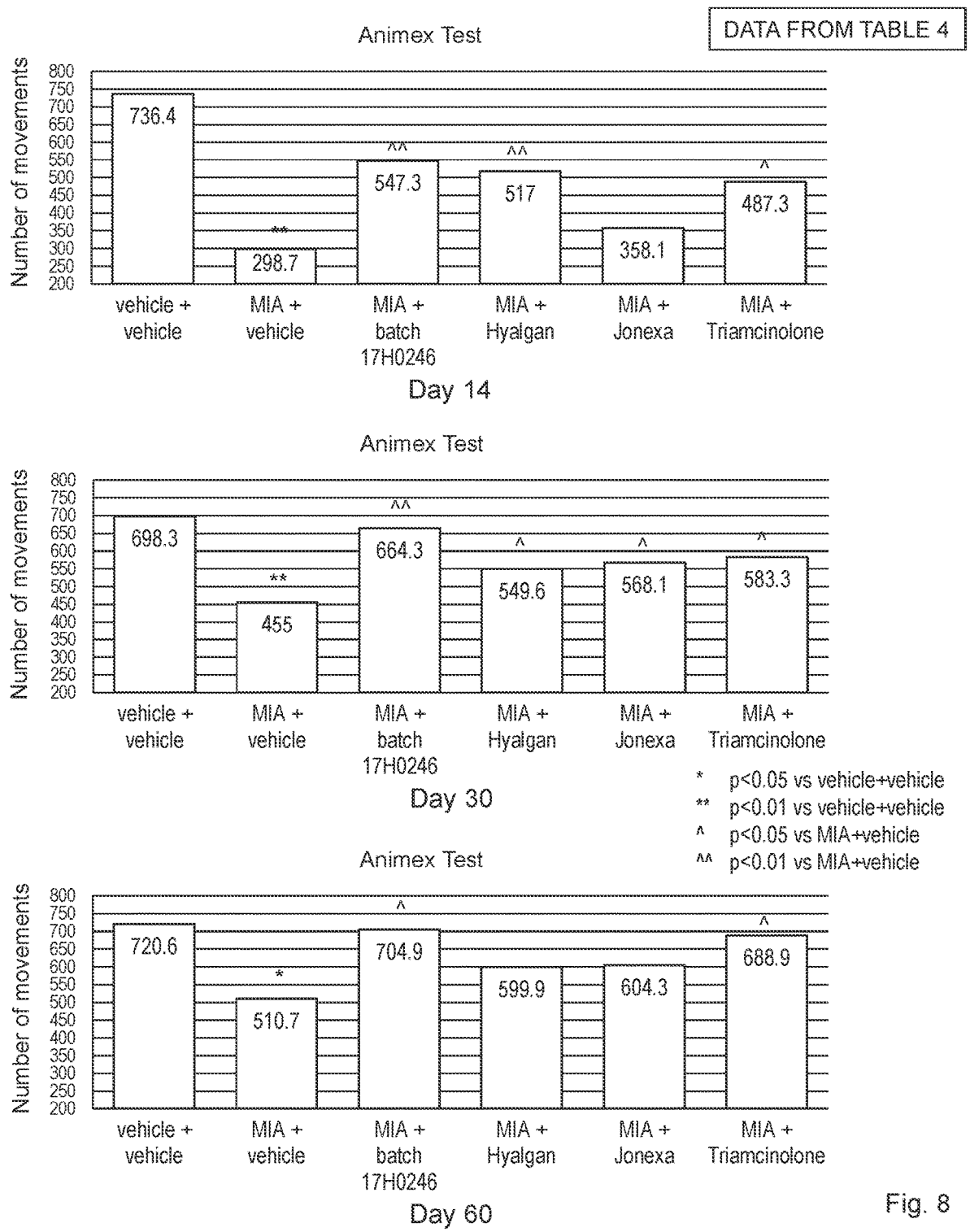
Figure 9:
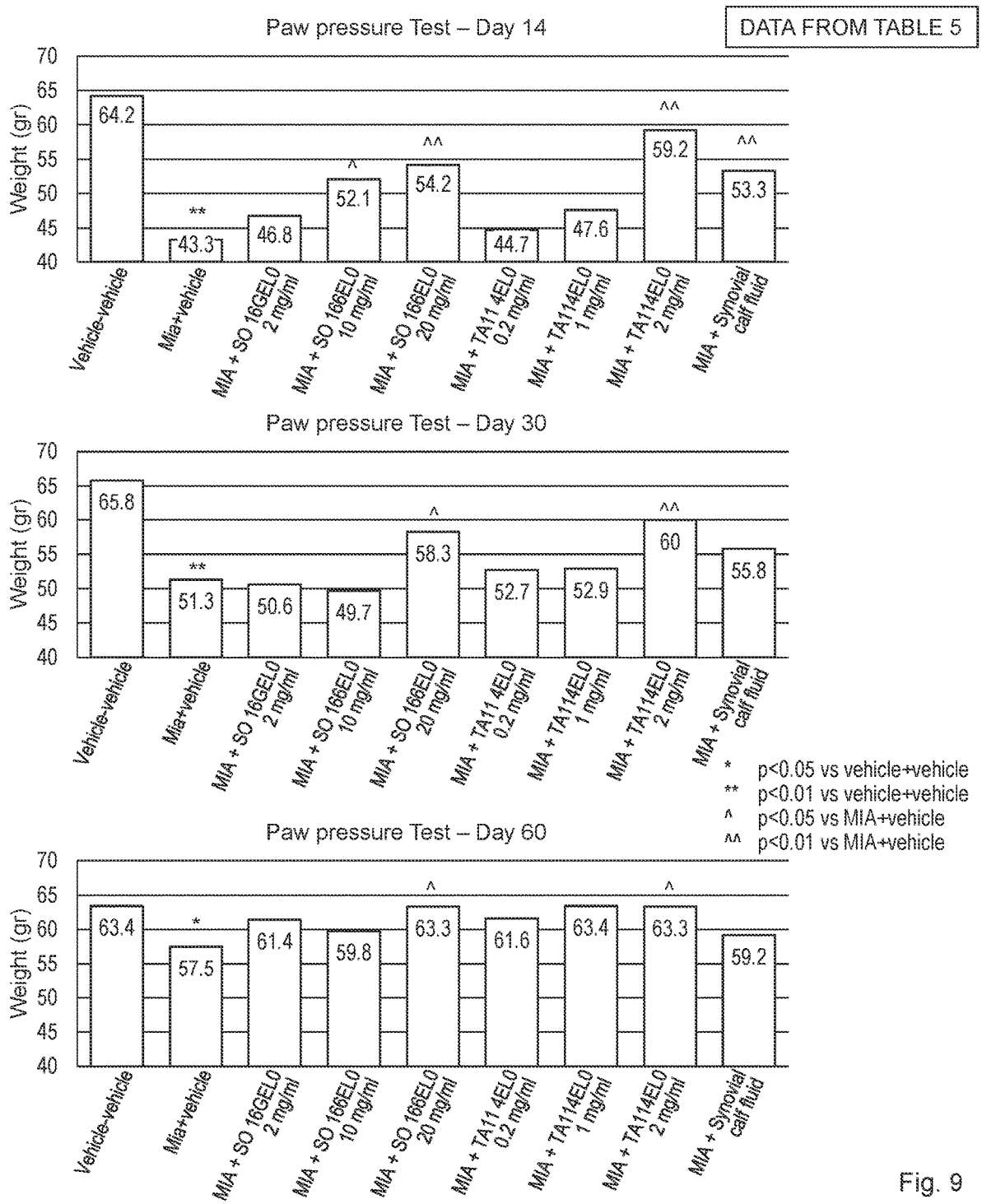
Figure 10:
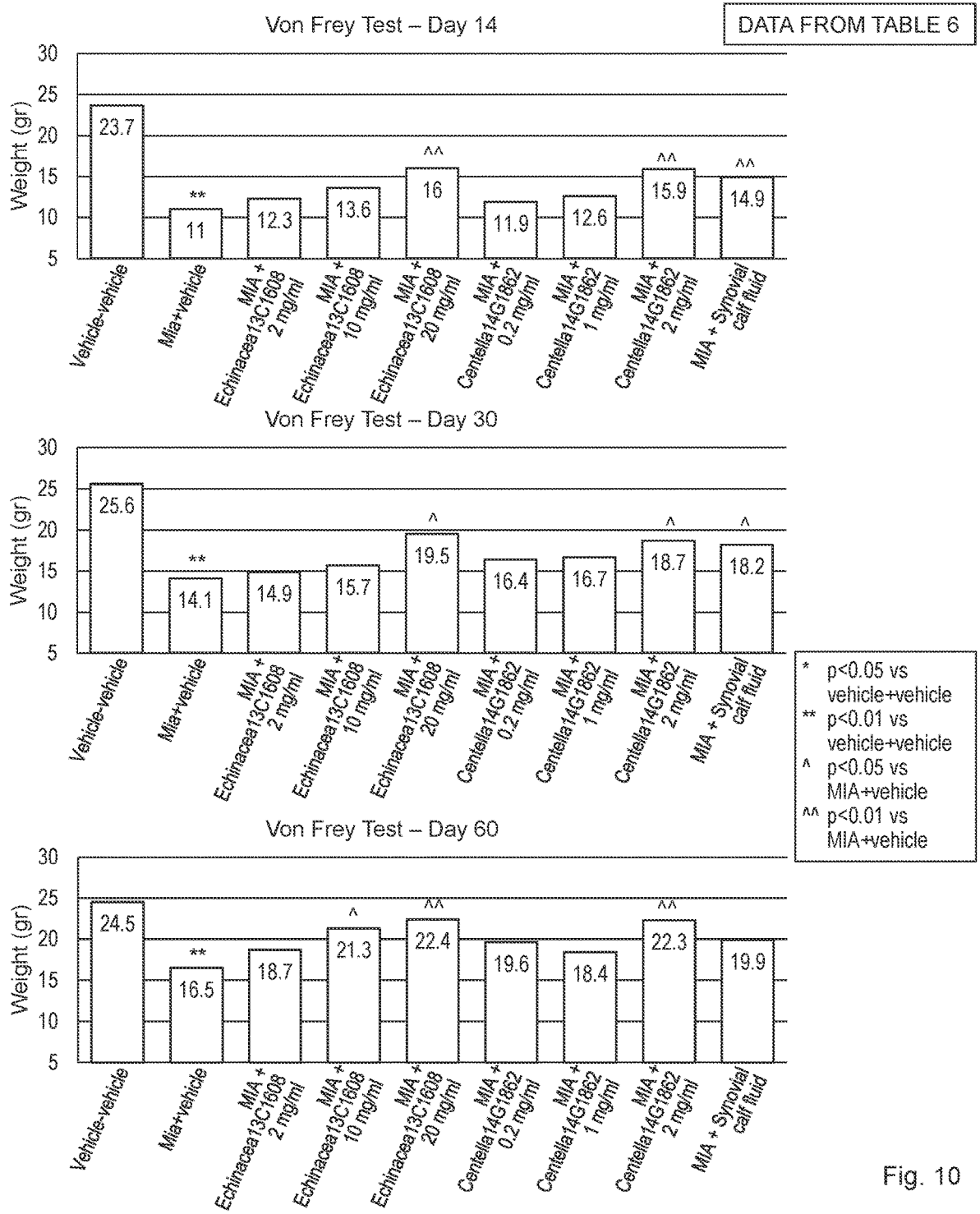
Figure 11:
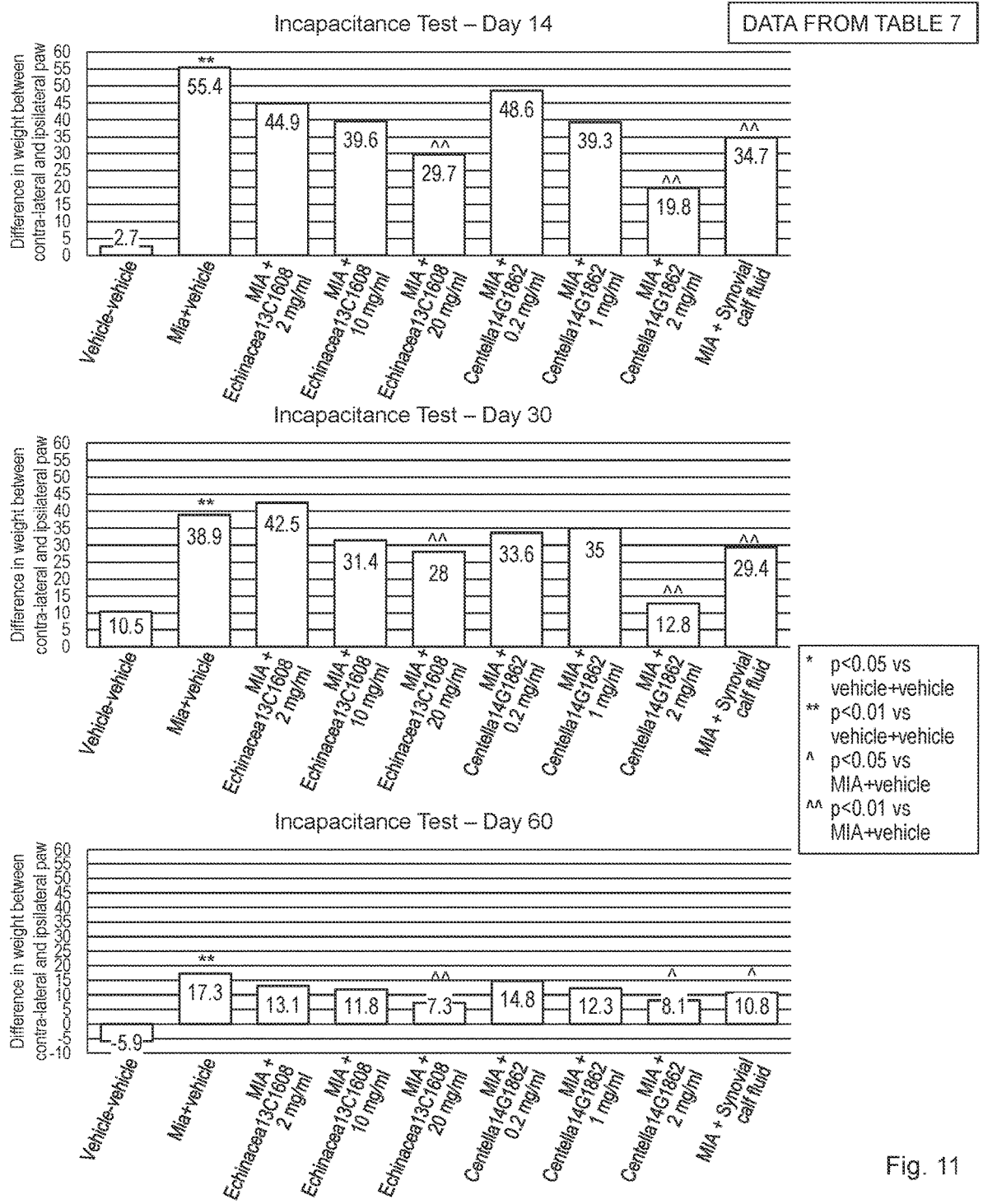
Figure 12:
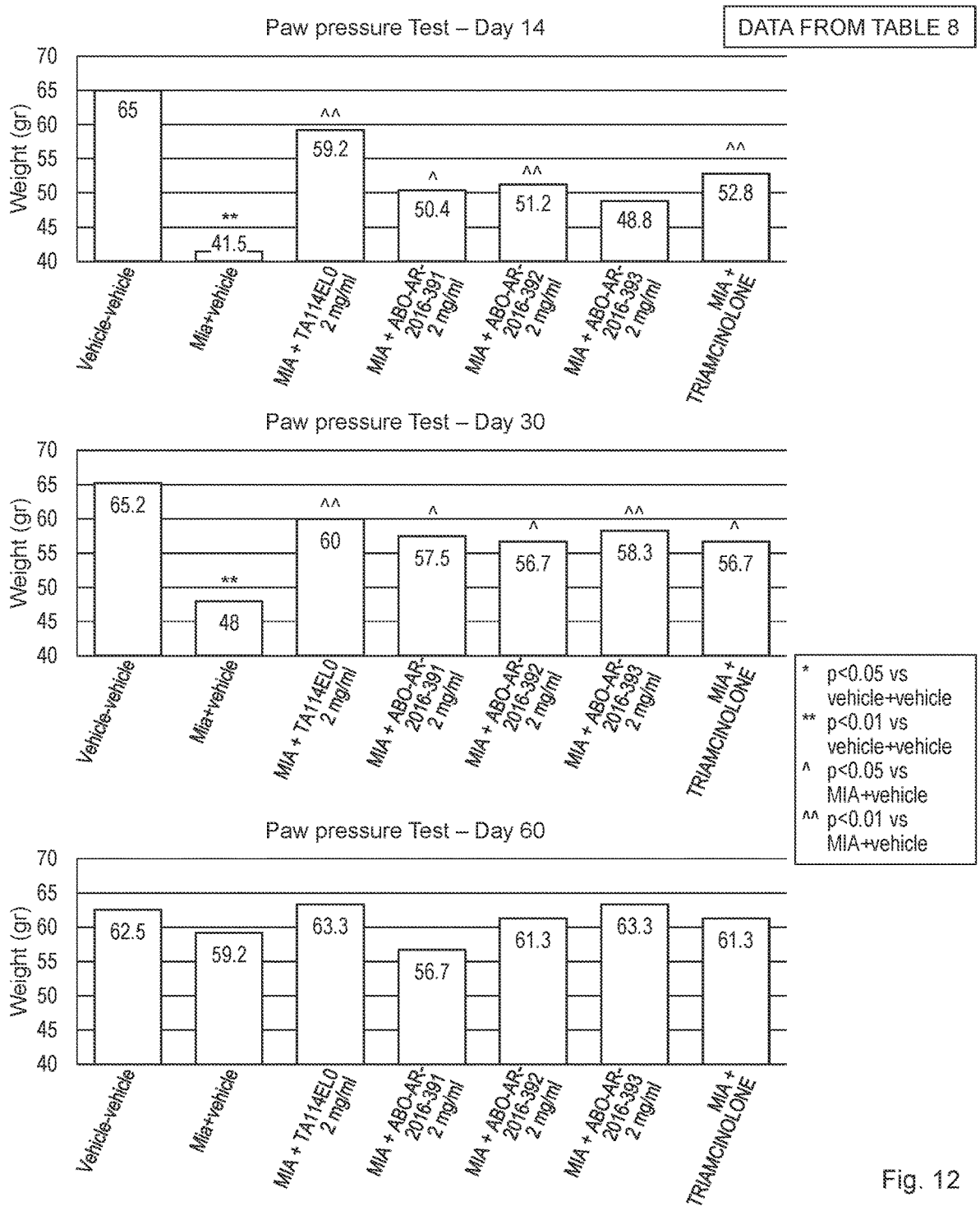
Figure 13:
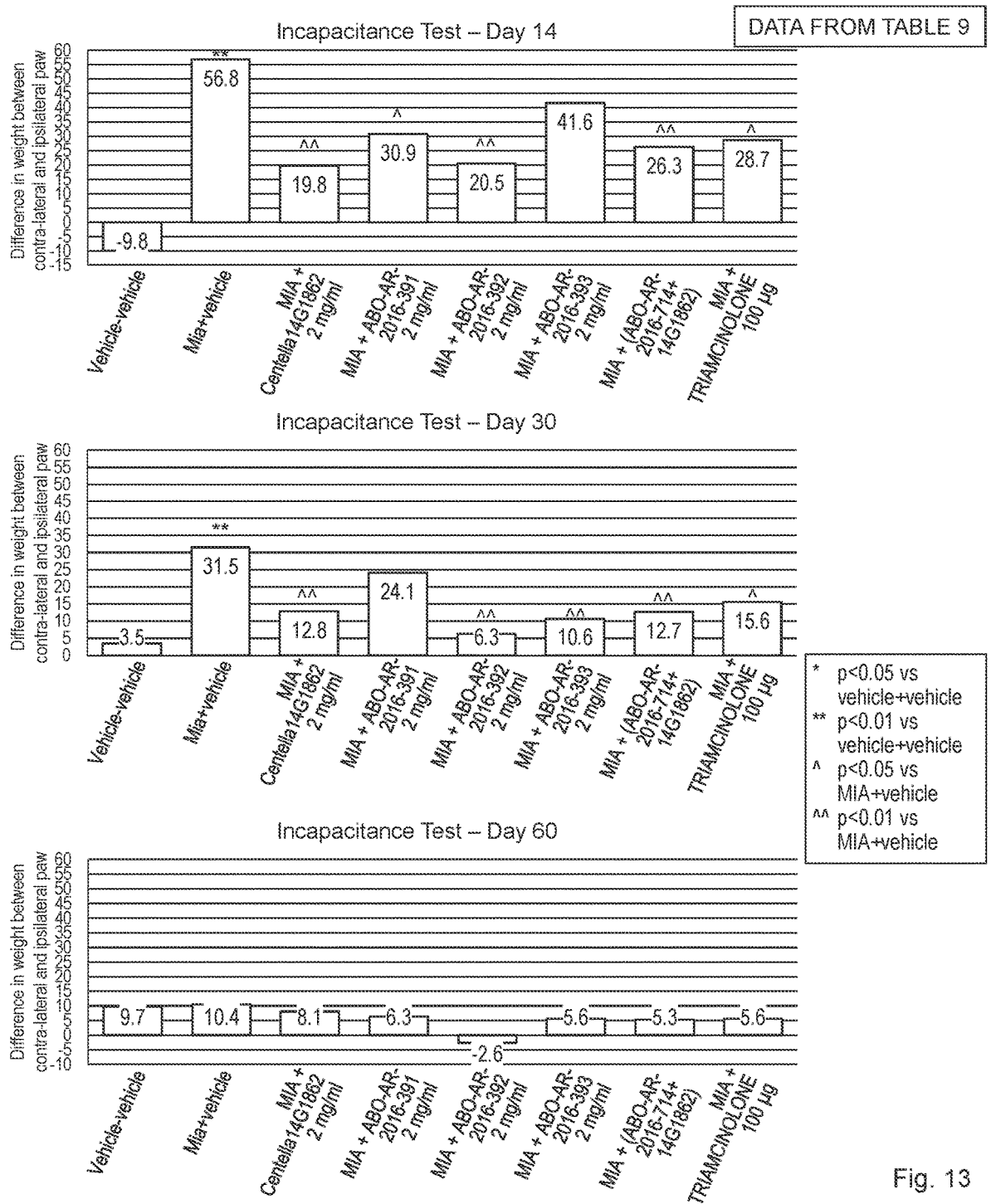
Figure 14:
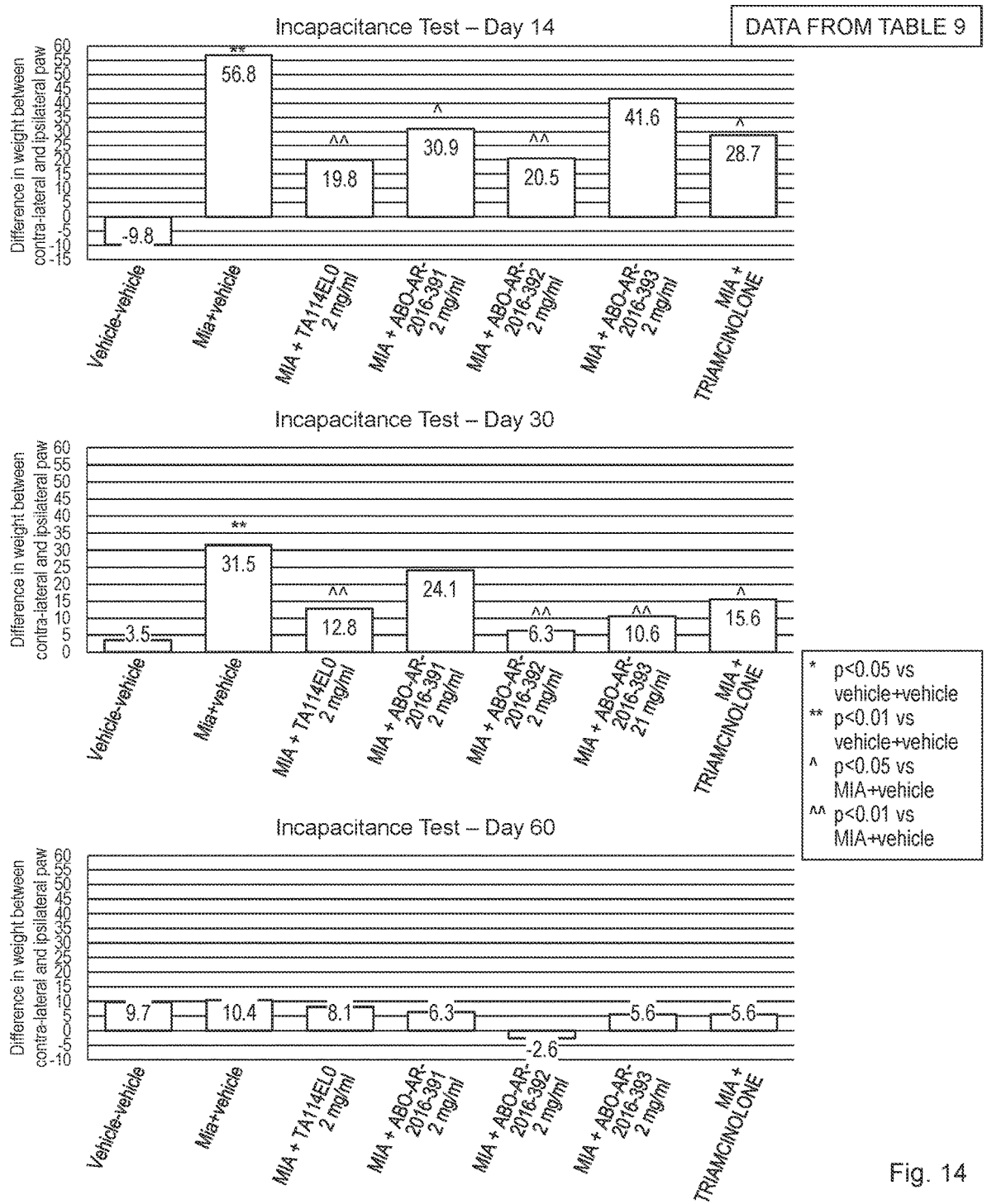
Figure 15:
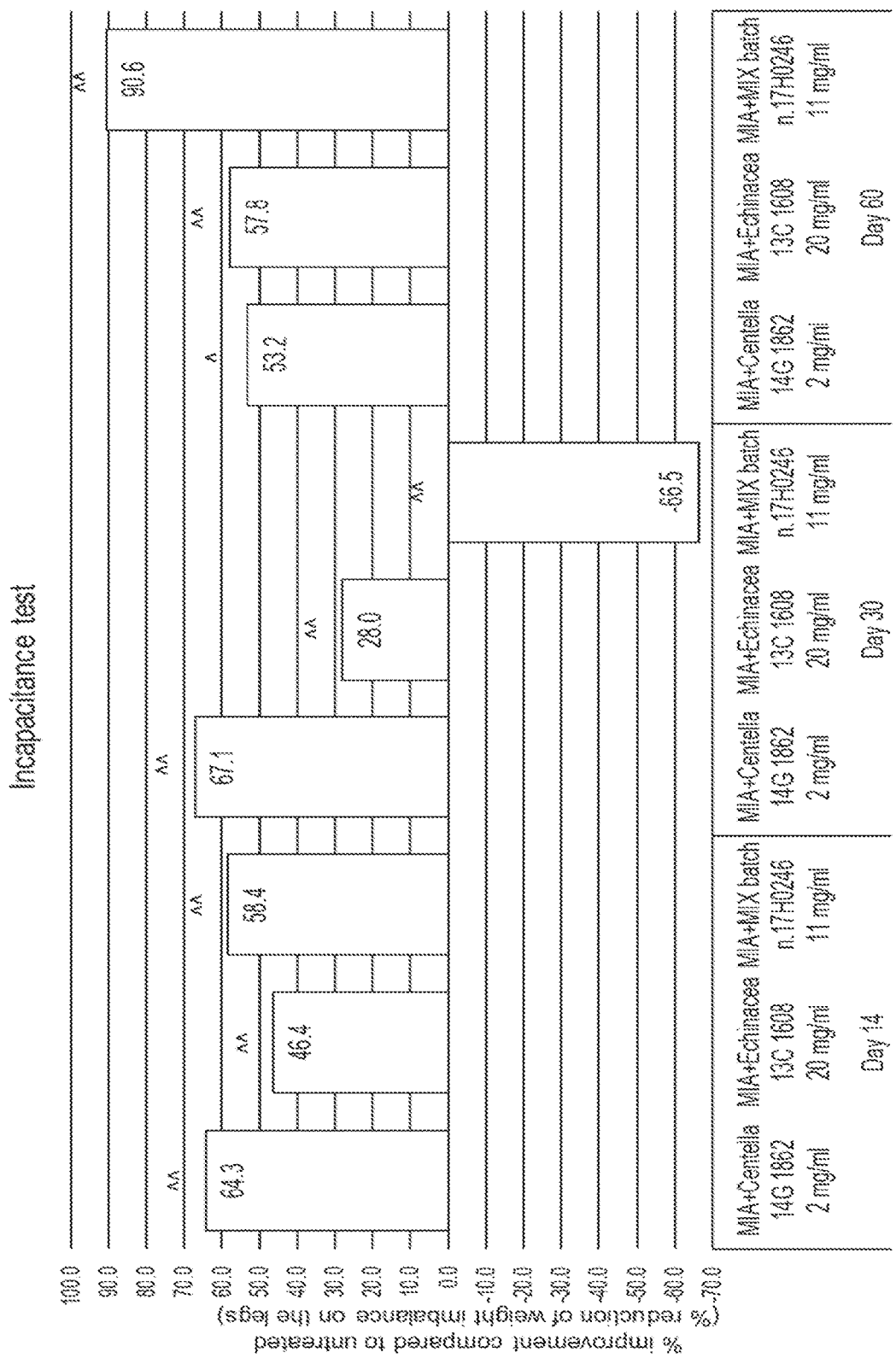
Figure 16:
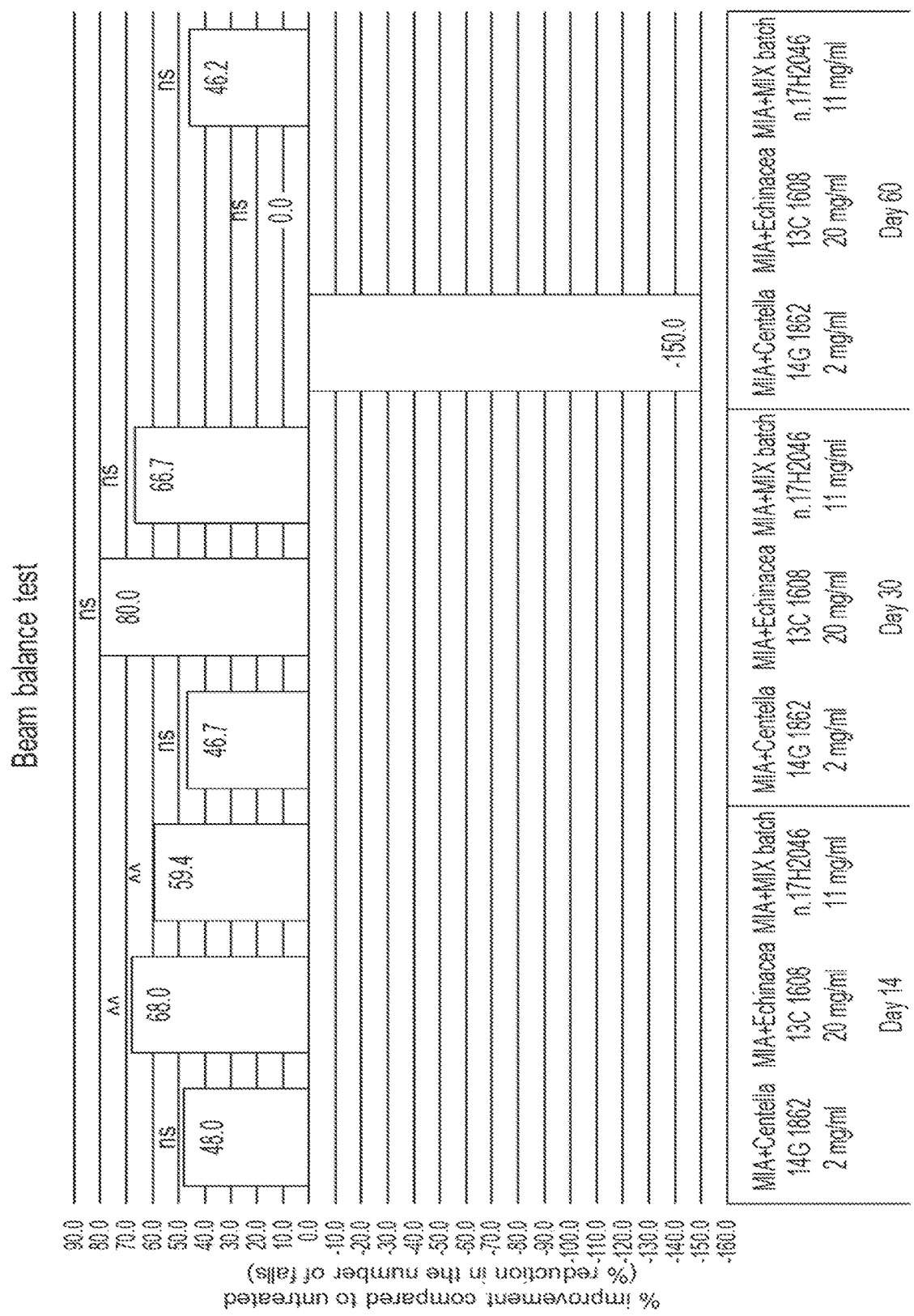
Figure 17:
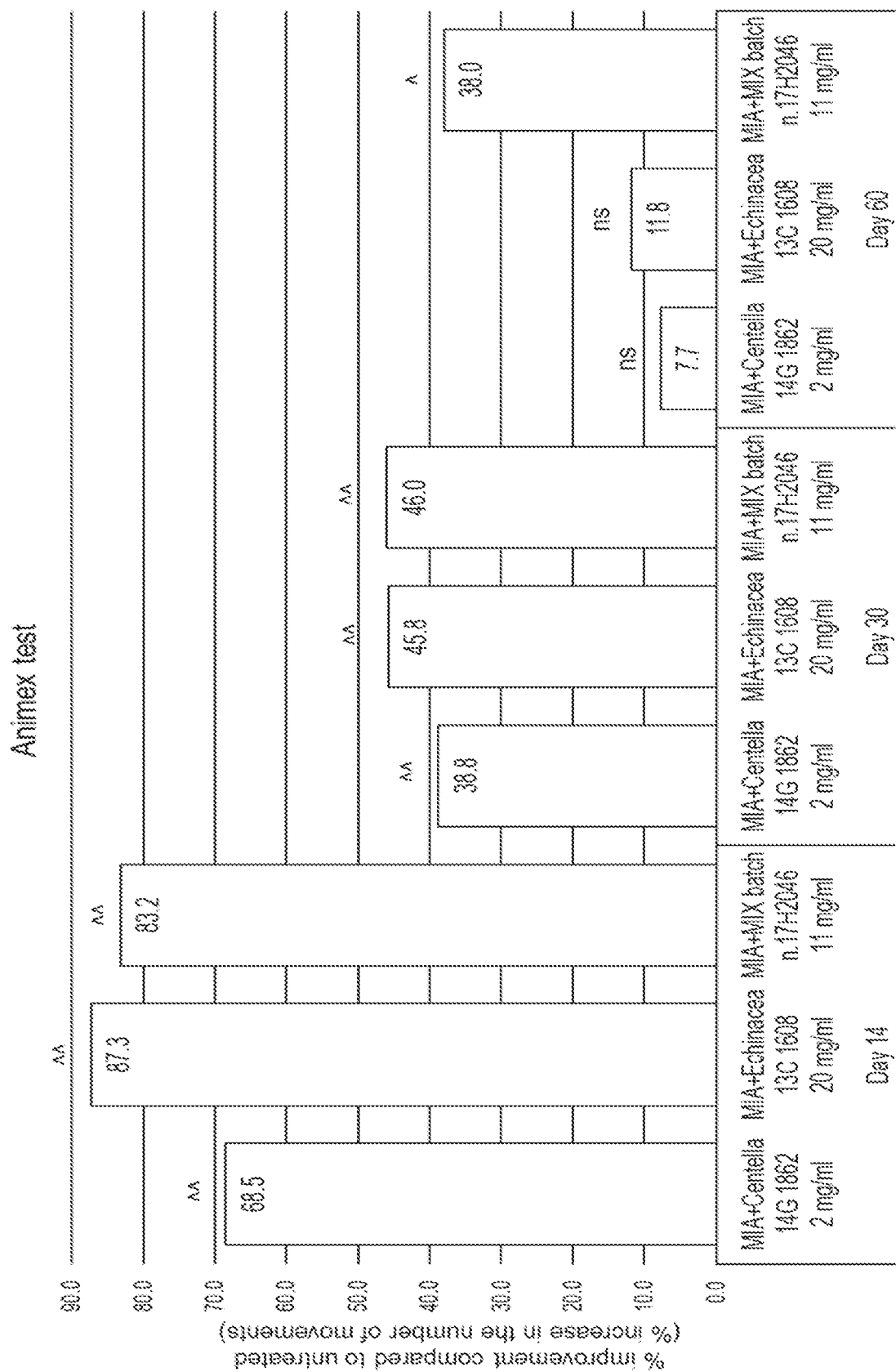

MIA+ABO-AR-2016-391: the treatment with ABO-AR-2016-391 improves in a statistically significant manner some parameters considered (Bone and cartilage erosion and joint space reduction). On the other parameters it shows effectiveness at 30 or 60 days of treatment (FIGS. 5 and 6).

MIA+ABO-AR-2016-392: the treatment with ABO-AR-2016-392 shows effectiveness at 30 and 60 days on all parameters analyzed, except in the presence of inflammatory infiltrate, where it shows activity only at 60 days. As regards cartilage and bone tissue erosion and joint space reduction, it proves significantly effective at all three experimental times (FIGS. 3 and 4).

MIA+ABO-AR-2016-393: the treatment with ABO-AR-2016-393 shows an effect on all morphological parameters analyzed, except on the presence of inflammatory infiltrate, where it has no effect. The improvement of morphological parameters induced by ABO-AR-2016-393 is however lower than that recorded with the other two fractions (FIGS. 3 and 4).

MIA+Triamcinolone: the treatment with triamcinolone shows a significant effectiveness in the reduction of inflammatory infiltrate and on erosion, both of cartilage and bone tissue. As regards synovial hyperplasia, fibrin deposition, synovial vascularization and joint space reduction, it demonstrates reduced effectiveness to 15- and 30-day timings and a more marked effectiveness after 60 days of treatment (FIGS. 3 and 4).

EXAMPLES

Examples of preparation of the therapeutically active principles of the invention are reported hereinafter. The technician in the field could use other analogous procedures or carry out modifications to the procedures reported below, obtaining extracts or fractions suitable to the carrying out of the invention on the basis of common general knowledge in the field.

1. Example of Preparation of Extract of *Centella asiatica* Fraction 14G1862

Dried and crumbled *Centella asiatica* leaves are subjected to extraction by ethanol 70% (ethanol:water 70:30 v/v), in a static extractor by percolate digestion, with the plant immersed in solvent and the solvent recycled bottom-to-top by a mechanical pump.

The drug-solvent ratio (DSR) is equal to 1:8, extraction temperature is of 50° C., extraction length is 6-8 hours. From the resulting mixture, the insoluble residue is separated from the soluble fraction by static decanting and subsequently by filtration on paper filter. The resulting solution is concentrated by ethanol evaporation, by use of a vacuum concentration system. Upon reaching a degree of concentration of 10:1, concentration is discontinued, and drying is completed by lyophilization. The lyophilized material constitutes the fraction of interest (DER 4-10:1).

The protocol described herein applies, mutatis mutandis, to the other alcoholic contents reported in the detailed part of the description.

2. Example of Preparation of Extract of *Echinacea purpurea* Fraction 13C1608

Dried and crumbled *Echinacea purpurea* tops are subjected to extraction by ethanol 45% (ethanol:water 45:55 v/v), in a static extractor by percolate digestion, with the plant immersed in solvent and the solvent recycled bottom-to-top by a mechanical pump.

The drug-solvent ratio (DSR) is equal to 1:8, extraction temperature is of 50° C., extraction length is 6-8 hours. From the resulting mixture, the insoluble residue is separated from the soluble fraction by static decanting and subsequently by filtration on paper filter. The resulting solution is concentrated by ethanol evaporation, by use of a vacuum concentration system. Upon reaching a degree of concentration of 10:1 concentration is discontinued, and drying is completed by lyophilization. The lyophilized material constitutes the fraction of interest (DER 4-10:1).

The protocol described herein applies, mutatis mutandis, to the other alcoholic contents reported in the detailed part of the description.

3. Example of Preparation of Fractions of *Centella asiatica* ABO-AR-2016-391, ABO-AR-2016-392, ABO-AR-2016-393

*Centella* leaves were fragmented and subjected to two steps of extraction in ethanol at decreasing concentration; performing a first step with ethanol 96%, plant parts treated with EtOH 96% were then subjected to a second step with ethanol 13%.

Extraction conditions of each extraction step were characterized by a length of time of 8 hours, a drug-solvent ratio (DSR) of 1:8, an extraction temperature of 40° C. The first alcoholic fraction obtained with the step with ethanol 96% was discarded. The second alcoholic fraction obtained with the step with ethanol 13% was subjected to concentration by ethanol evaporation, by use of vacuum distillation system according to standard protocol, thereby obtaining, after ethanol elimination, a concentrated aqueous extract.

The concentrated aqueous extract obtained was filtered on a plate filter, with a paper filter having a 25-micrometer cutoff. Part of this concentrate was subjected to drying by lyophilization, providing the corresponding lyophilized fraction (ABO-AR-2016-391) (DER 5-10:1).

The filtered concentrated aqueous extract obtained as described above was subjected to a step of filtration on a membrane with a cutoff of 150-300 Da, according to standard methodologies, providing the permeate fraction and the retentate fraction. Said fractions were subjected to drying by lyophilization, providing the corresponding lyophilized fractions: permeate (DER 10-30:1) (ABO-AR-2016-392) and retentate (DER 5-20:1) (ABO-AR-2016-393).

The protocol described herein applies, mutatis mutandis, to the other membranes provided in the detailed part of the description.

4. Example of Preparation of Formulation According to the Invention

1. The lyophilized extracts were solubilized in water with NaCl, heating the mixture at a temperature comprised between 30 and 80° C., preferably between 30 and 70° C., 40 and 50° C. for a period of time comprised between 4 and 8 hours in order to foster extract solubilization.
2. The mixture obtained at the preceding point, after cooling, was filtered to eliminate any undissolved particles of extract, and then dried, preferably by lyophilization and resuspended in a suitable pharmaceutically acceptable carrier.
3. At this stage, oily substances and emulsifiers may be added if necessary, if surface-activated systems are to be obtained.
4. The mixture of extracts was additioned with the other excipients soluble in water, such as buffers, isotonic agents.
5. The pH of the prepared solution is measured and suitably corrected if necessary.
6. The solution so obtained was sterilized by sterilizing filtration or moist heat (steam) in autoclave.

The invention claimed is:

1. A parenteral composition consisting essentially of:
an extract of *Centella asiatica* and an extract of *Echinacea purpurea*, and
at least one pharmaceutically acceptable carrier.

2. The parenteral composition according to claim 1, wherein said extract of *Centella asiatica* is an extract from leaves of a plant.

3. The parenteral composition according to claim 1, wherein said extract of *Echinacea purpurea* is an extract from aerial parts of a plant.

4. The parenteral composition according to claim 1, wherein said extract of *Centella asiatica* and/or said extract of *Echinacea purpurea* is a lyophilized extract in hydroalcoholic solution.

5. The parenteral composition according to claim 4, wherein said extracts are blended in a ratio from 7:3 and 9.5:0.5 *Centella:Echinacea*, and coextracted and lyophilized after incubation in water and 0.8-4% NaCl at 30-70° C. for 4-8 hours and filtration.

6. The parenteral composition according to claim 1 that comprises 0.08-2% w/w total phenols when said composition is in a lyophilized form.

7. The parenteral composition according to claim 1 that comprises 1-2% polysaccharides with a molecular weight of greater than 2000 daltons when said composition is in lyophilized form.

8. The parenteral composition according to claim 1 that comprises 0.002-1% w/w total tannins when said composition is in lyophilized form.

9. A parenteral composition comprising 0.08-2.0% w/w of total phenols, 0.002-1% w/w of total tannins, 1%-2% w/w of polysaccharides with a molecular weight above 20000 Da, when in lyophilized form, and at least one pharmaceutically acceptable carrier, wherein said phenols, tannins, polysaccharides are derived from *Centella asiatica* and *Echinacea purpurea*.

10. The parenteral composition according to claim 1, wherein the extract of *Centella* and the extract of *Echinacea purpurea* are the sole therapeutically active agents.

11. A kit comprising the parenteral composition according to claim 10, wherein the therapeutically active agents are provided in aliquots in lyophilized form and said at least one pharmaceutically acceptable carrier is provided in separate aliquots.

12. The parenteral composition according to claim 10, wherein the therapeutically active principle is dissolved in said pharmaceutically acceptable carrier.

13. The composition according to claim 1, wherein said pharmaceutically acceptable carrier is selected from solvents, emulsifiers, buffering agents, pH correctors, antioxidants, preservatives, and/or osmotic agents.

14. The parenteral composition according to claim 13, wherein said solvents are selected from one or more of: water, polyvinylpyrrolidone, and isotonic saline solutions; and/or
said emulsifiers are selected from one or more of: lecithins, and ethoxylated derivatives of fatty acids; and/or
said buffering agents are selected from one or more of: citric acid and its sodium salts, phosphoric acid and its sodium salts, and acetic acid and its sodium salts; and/or
said pH correctors are selected from one or more of: hydrochloric acid and sodium hydroxide; and/or
said antioxidants are selected from one or more of: sodium bisulfate, and sodium metabisulfite, ethylenediamine tetraacetic acid and its sodium salts; and/or
said preservatives are selected from one or more of: benzyl alcohol, methyl p-hydroxybenzoate, benzalkonium chloride, and benzethonium chloride: and/or
said osmotic agents are selected from one or more of: sodium chloride, sugars, mannitol, dextrose, and glucose.

15. A method of treating disorders affecting articular cartilage in vertebrate animals comprising administering the parental composition of claim 1 to said animals.

16. The method of claim 15, wherein said disorders affecting articular cartilage are selected from arthritis, osteoarthritis, inflammation of the joints, cartilage damage caused by trauma, degeneration of spinal discs, rheumatoid arthritis.

17. The method of claim 15, wherein said composition is administered to said animal by infiltration/articular injection.

18. A process for preparing a parenteral composition comprising an extract of *Centella asiatica*, an extract of *Echinacea purpurea* and at least one pharmaceutically acceptable carrier, wherein
a) *Centella asiatica* leaves are subjected to one or more steps of extraction with hydroalcoholic mixtures, and the extract so obtained is subjected to lyophilization;
b) *Echinacea purpurea* aerial parts are subjected to one or more steps of extraction with hydroalcoholic mixtures and the extract so obtained is subjected to lyophilization;
c) the lyophilized extracts obtained in a) and b) in any order are mixed in a ratio extract of *Centella asiatica*: extract of *Echinacea purpurea* comprised between 8:2 and 0.5:9.5
d) the extracts so mixed are resuspended in water containing 0.8-4% sodium chloride
e) the mixture so obtained is brought to a temperature comprised between 30 and 70° C. for a time comprised between 4-8 hours, and subsequently subjected to filtering or decanting,
f) the filtrate or the supernatant obtained in e) are lyophilized; and
g) the lyophilized coextract obtained in f) is resuspended in one or more pharmaceutically acceptable carriers.

19. The process according to claim 18, wherein said extract at a) is a fraction of extract soluble in a hydroalcoholic solution wherein alcohol is from 65% to 75% v/v, a fraction of extract not soluble in ethanol 90-96% v/v and soluble in ethanol 10-20% v/v or mixtures thereof.

20. The process according to claim 18, wherein said extract in b) is a fraction of extract soluble in a hydroalcoholic solution wherein said alcohol is from 40% to 50% v/v.

21. A parenteral composition obtainable by the process according to claim 18.

22. A method of treating disorders affecting articular cartilage in vertebrate animals comprising administering the parenteral composition of claim 21 to said animal.

23. The method of claim 22, wherein said disorders affecting articular cartilage are selected from arthritis, osteoarthritis, inflammation of the joints, cartilage damage caused by trauma, degeneration of spinal discs, rheumatoid arthritis.

24. The method of claim 22, wherein said composition is administered to said animal by means of infiltration/articular injection.

25. A parenteral composition comprising an extract of *Centella asiatica*, an extract of *Echinacea purpurea*, and at least one pharmaceutically acceptable carrier;
   wherein the extract of *Centella* and the extract of *Echinacea purpurea* are the sole therapeutically active agents.

* * * * *